US008327367B2

(12) United States Patent  
Takano et al.

(10) Patent No.: US 8,327,367 B2  
(45) Date of Patent: *Dec. 4, 2012

(54) INFORMATION SERVICE PROVIDING SYSTEM, INFORMATION SERVICE PROVIDING DEVICE, AND METHOD THEREFOR

(75) Inventors: Kosuke Takano, Kanagawa (JP); Naofumi Yoshida, Kanagawa (JP); Shuichi Kurabayashi, Kanagawa (JP)

(73) Assignee: Empire Technology Development LLC, Wilmington, DE (US)

( * ) Notice: Subject to any disclaimer, the term of this patent is extended or adjusted under 35 U.S.C. 154(b) by 279 days.

This patent is subject to a terminal disclaimer.

(21) Appl. No.: 12/665,304

(22) PCT Filed: Mar. 5, 2009

(86) PCT No.: PCT/JP2009/054140  
§ 371 (c)(1),  
(2), (4) Date: Dec. 17, 2009

(87) PCT Pub. No.: WO2010/100735  
PCT Pub. Date: Sep. 10, 2010

(65) Prior Publication Data  
US 2011/0231863 A1    Sep. 22, 2011

(51) Int. Cl.  
*G06F 9/46* (2006.01)  
*G06F 11/30* (2006.01)  
*G06F 11/00* (2006.01)  
*G01L 15/00* (2006.01)  
*H03F 1/26* (2006.01)

(52) U.S. Cl. ........ 718/102; 718/103; 718/106; 718/107; 702/121; 702/183; 702/184; 702/188; 702/189

(58) Field of Classification Search ........................ None  
See application file for complete search history.

(56) References Cited

U.S. PATENT DOCUMENTS

| 6,886,045 | B1 * | 4/2005 | Halasz et al. ................. 709/245 |
| 8,184,170 | B2 | 5/2012 | Yamaji |
| 2002/0084675 | A1 | 7/2002 | Buchanan et al. |
| 2003/0013438 | A1 | 1/2003 | Darby |
| 2003/0069752 | A1 | 4/2003 | LeDain et al. |
| 2004/0040771 | A1 | 3/2004 | Ploucha |

(Continued)

FOREIGN PATENT DOCUMENTS

JP        09-296772        11/1997

(Continued)

OTHER PUBLICATIONS

Decision of Rejection for JP 2009-545027 mailed Jun. 4, 2010 (with English translation).

(Continued)

*Primary Examiner* — Camquy Truong  
(74) *Attorney, Agent, or Firm* — Foley & Lardner LLP

(57) ABSTRACT

An information service providing device selects a combination, all sensors contained in which are available and which has the highest priority, from within the combinations of sensors, which are for implementing an information service. In addition, the information service providing device selects an appropriate parameter for the sensors and processing program selected so as to be provided appropriately in response to the environment in which an information service has been implemented, and sets the parameter to these. By selecting sensors and processing program, and setting parameters, the information service providing device with only the receipt of the designation of desired information service by a user, various information services by appropriately combining various kinds of sensors and a plurality of processing programs.

12 Claims, 21 Drawing Sheets

U.S. PATENT DOCUMENTS

| | | |
|---|---|---|
| 2005/0011129 A1 | 1/2005 | Vassy |
| 2006/0056625 A1 | 3/2006 | Nakabayashi et al. |
| 2006/0109734 A1 | 5/2006 | Fukuda et al. |
| 2006/0287889 A1 | 12/2006 | Brown |
| 2007/0218862 A1 | 9/2007 | Tatman et al. |
| 2008/0194925 A1 | 8/2008 | Alsafadi et al. |
| 2008/0225137 A1 | 9/2008 | Kubo et al. |
| 2008/0239083 A1 | 10/2008 | Kusaka et al. |
| 2008/0256214 A1 | 10/2008 | Halasz et al. |
| 2008/0270922 A1 | 10/2008 | Kii et al. |
| 2009/0069642 A1 | 3/2009 | Gao et al. |
| 2009/0324211 A1 | 12/2009 | Strandell et al. |
| 2010/0234694 A1 | 9/2010 | Takano et al. |
| 2011/0002223 A1 | 1/2011 | Gross |
| 2011/0023863 A1 | 2/2011 | Andretich |
| 2011/0040574 A1 | 2/2011 | Fung et al. |
| 2011/0231863 A1 | 9/2011 | Takano et al. |

FOREIGN PATENT DOCUMENTS

| | | |
|---|---|---|
| JP | 2001-216315 | 8/2001 |
| JP | 2002-015068 | 1/2002 |
| JP | 2002-304201 | 10/2002 |
| JP | 2002-366653 | 12/2002 |
| JP | 2004-194174 | 7/2004 |
| JP | 2005-049199 | 2/2005 |
| JP | 2005-085871 | 3/2005 |
| JP | 2006-060438 | 3/2006 |
| JP | 2006-236176 | 9/2006 |
| JP | 2006-238237 | 9/2006 |
| JP | 2006-295823 | 10/2006 |
| JP | 2008-128927 | 5/2008 |
| JP | 2008-306464 | 12/2008 |
| WO | WO 03/017159 | 2/2003 |
| WO | WO 2006/018962 | 2/2006 |

OTHER PUBLICATIONS

Notice of Reasons for Rejection for JP 2009-545026 mailed Dec. 1, 2009 (with English translation).

Decision of Rejection for JP 2009-545026 mailed Jun. 4, 2010 (with English translation).

Kurabayashi, Shuichi et al., "Active Multidatabase System for Mobile Computing Environment," *Information Processing Society of Japan*, The Special Interest Group Technical Reports of IPSJ 2000-DBS-122, 2000, pp. 463-470 (with English abstract).

Kurabayashi, Shuichi et al., "A Multidatabase System Architecture for Integrating Heterogeneous Databases with Meta-Level Active Rule Primitives," *Proceedings of the 20th IASTED International Conference on Applied Informatics*, 2002, pp. 378-387.

Notice of Reasons for Rejection for JP 2009-545027 mailed Dec. 1, 2009 (with English translation).

International Preliminary Report on Patentability for PCT/JP2009/054139 mailed Oct. 27, 2011.

International Preliminary Report on Patentability for PCT/JP2009/054140 dated Oct. 28, 2011.

International Search Report for PCT/JP2009/054139 mailed Apr. 28, 2009.

International Search Report for PCT/JP2009/054140 mailed Apr. 28, 2009.

International Search Report with translation from PCT/EP2008/058094 dated Sep. 1, 2008 (4 pages).

Final Rejection for Japanese Pat. Appln. No. 2009-060545, mailed on Sep. 15, 2009, 6 pp. (including English Translation).

Notice of Rejection for Japanese Pat. Appln. No. 2009-060545, mailed on Apr. 21, 2009, 4 pp. (including English Translation).

Kurabayashi, et al., "A Multidatabase System Architecture for Integrating Heterogeneous Databases with Meta-Level Active Rule Primitives," Proceedings of the 20th IASTED International Conference on Applied Informatics, Feb. 2002, 10 pages.

Kurabayashi, et al., "Active Multidatabase System for Mobile Computing Environment," Institute of Electronics, Information and Communication Engineers, vol. 100, No. 228, 2000, 9 pages.

Non-final Office Action received for U.S. Appl. No. 12/665,107 dated Jul. 23, 2012.

Notice of Allowance received for U.S. Appl. No. 12/568,188 dated Jan. 4, 2011.

U.S. Appl. No. 12/640,967, DTD Oct. 2, 2012.

\* cited by examiner

FIG. 6

| SERVICES | SENSORS FOR SERVICE AND THEIR PRIORITIES ||||||||||||||| SETS OF MODULES FOR SERVICES | PRIORITIES OF SERVICES |
| --- | 162 | 164 | 166 | 168 | 170 | 172 | 174 | 176 | 178 | 180 | 182 | 184 | 186 | 190-1 | 190-n | --- | --- |
| S#1 (HEALTH CHECK) | 0 | 3 | 1 | 0 | 0 | 2 | 0 | 0 | 0 | 0 | 0 | 0 | 0 | 0 | 0 | MS#1 | 2 |
| S#i (NAVIGATION) | 0 | 0 | 0 | 0 | 0 | 0 | 0 | 1 | 2 | 2 | 2 | 0 | 0 | 0 | 0 | MS#i | 1 |
| S#i+1 (IMAGE INFORMATION) | 0 | 0 | 0 | 0 | 0 | 0 | 0 | 1 | 2 | 2 | 2 | 0 | 0 | 0 | 0 | MS#i+1 | 4 |
| S#j | $N_{j1}$ | $N_{j2}$ | $N_{j3}$ | $N_{j4}$ | $N_{j5}$ | $N_{j6}$ | $N_{j7}$ | $N_{j8}$ | $N_{j9}$ | $N_{j10}$ | $N_{j11}$ | $N_{j12}$ | $N_{j13}$ | $N_{j14}$ | $N_{jk}$ | MS#j | 1 |
| S#n | $N_{n1}$ | $N_{n2}$ | $N_{n3}$ | $N_{n4}$ | $N_{n5}$ | $N_{n6}$ | $N_{n7}$ | $N_{n8}$ | $N_{n9}$ | $N_{n10}$ | $N_{n11}$ | $N_{n12}$ | $N_{n13}$ | $N_{n14}$ | $N_{nk}$ | MS#n | 3 |

FIG. 7

| SERVICES | PARAMETERS FOR MODULES | | | | | | | |
|---|---|---|---|---|---|---|---|---|
| | #1 | #2 | ... | #i | #(i+1) | #(i+2) | #(i+3) | ... | #n |
| S#1 (HEALTH CHECK) | P'₁₁ | P'₁₂ | | - | - | - | | |
| ... | | | | | | | | |
| S#i (NAVIGATION) | - | - | | P'ᵢⱼ | P'ᵢ(ⱼ+1) | P'ᵢ(ⱼ+2) | | |
| S#i+1 (IMAGE INFORMATION) | - | - | | P'ᵢⱼ | P'ᵢ(ⱼ+1) | | P'ᵢ(ⱼ+3) | |
| ... | | | | | | | | |
| S#j | P'ₙ₁ | P'ₙ₂ | | P'ₙⱼ | P'ₙ(ⱼ+1) | P'ₙ(ⱼ+2) | | P'ₙₙ |

FIG. 8

| SERVICES | PARAMETERS FOR SENSORS | | | | | | | | | | | | | | | |
|---|---|---|---|---|---|---|---|---|---|---|---|---|---|---|---|---|
| | 160 | 162 | 166 | 168 | 170 | 172 | 174 | 176 | 178 | 180 | 182 | 184 | 186 | 190-1 | ... | 190-n |
| S#1 (HEALTH CHECK) | - | $P_{12}$ | $P_{13}$ | - | - | $P_{16}$ | - | - | - | - | - | - | - | - | | - |
| S#i (NAVIGATION) | - | - | - | - | - | - | - | $P_{i8}$ | $P_{i9}$ | $P_{i10}$ | $P_{i11}$ | $P_{i12}$ | - | - | | - |
| S#i+1 (IMAGE INFORMATION) | - | - | - | - | - | - | - | $P_{i8}$ | $P_{i9}$ | $P_{i10}$ | $P_{i11}$ | $P_{i12}$ | - | - | | - |
| S#j | $P_{j1}$ | $P_{j2}$ | $P_{j3}$ | $P_{j4}$ | $P_{j5}$ | $P_{j6}$ | $P_{j7}$ | $P_{j8}$ | $P_{j9}$ | $P_{j10}$ | $P_{j11}$ | $P_{j12}$ | $P_{j13}$ | $P_{j14}$ | | $P_{jk}$ |
| S#n | $P_{n1}$ | $P_{n2}$ | $P_{n3}$ | $P_{n4}$ | $P_{n5}$ | $P_{n6}$ | $P_{n7}$ | $P_{n8}$ | $P_{n9}$ | $P_{n10}$ | $P_{n11}$ | $P_{n12}$ | $P_{n13}$ | $P_{n14}$ | | $P_{nk}$ |

FIG. 15

| SERVICES | SENSORS FOR SERVICE AND THEIR PRIORITIES | | | | | | | | | | | | | | | | SETS OF MODULES FOR SERVICES | PRIORITIES OF SERVICES |
|---|---|---|---|---|---|---|---|---|---|---|---|---|---|---|---|---|---|---|
| | 162 | 164 | 166 | 168 | 170 | 172 | 174 | 176 | 178 | 180 | 182 | 184 | 186 | 190-1 | | 190-n | | |
| S#1 (HEALTH CHECK) | 0 | 3 | 1 | 0 | 0 | 2 | 0 | 0 | 0 | 0 | 0 | 0 | 0 | 0 | | 0 | MS#1 | 2 |
| S#i (NAVIGATION) | 0 | 0 | 0 | 0 | 0 | 0 | 0 | 1 | 2 | 2 | 2 | 0 | 0 | 0 | | 0 | MS#i | 1 |
| S#i+1 (IMAGE INFORMATION) | 0 | 0 | 0 | 0 | 0 | 0 | 0 | 1 | 2 | 2 | 2 | 0 | 0 | 0 | | 0 | MS#i | 1 |
| S#m (WEB BROWER) | 1/2 | 1/2 | 0 | 1 | 0 | 0 | 0 | 0 | 0 | 0 | 0 | 0 | 1 | 0 | | 0 | MS#j | 1 |
| S#n | $N_{n1}$ | $N_{n2}$ | $N_{n3}$ | $N_{n4}$ | $N_{n5}$ | $N_{n6}$ | $N_{n7}$ | $N_{n8}$ | $N_{n9}$ | $N_{n10}$ | $N_{n11}$ | $N_{n12}$ | $N_{n13}$ | $N_{n14}$ | | $N_{nk}$ | MS#n | 3 |

FIG. 16

| SERVICES | PARAMETERS FOR SENSORS | | | | | | | | | | | | | | | |
|---|---|---|---|---|---|---|---|---|---|---|---|---|---|---|---|---|
| | 160 | 162 | 166 | 168 | 170 | 172 | 174 | 176 | 178 | 180 | 182 | 184 | 186 | 190-1 | | 190-n |
| S#1 (HEALTH CHECK) | - | $P_{12}$ | $P_{13}$ | - | - | $P_{16}$ | - | - | - | - | - | - | - | - | | - |
| S#i (NAVIGATION) | - | - | - | - | - | - | - | $P_{i8}$ | $P_{i9}$ | $P_{i10}$ | $P_{i11}$ | $P_{i12}$ | - | - | | - |
| S#i+1 (IMAGE INFORMATION) | - | - | - | - | - | - | - | $P_{i8}$ | $P_{i9}$ | $P_{i10}$ | $P_{i11}$ | $P_{i12}$ | - | - | | - |
| S#m (WEB BROWSER) | $P_{m1}$ | $P_{m2}$ | - | $P_{m4}$ | - | - | - | - | - | - | - | - | $P_{m13}$ | - | | - |
| S#n | $P_{n1}$ | $P_{n2}$ | $P_{n3}$ | $P_{n4}$ | $P_{n5}$ | $P_{n6}$ | $P_{n7}$ | $P_{n8}$ | $P_{n9}$ | $P_{n10}$ | $P_{n11}$ | $P_{n12}$ | $P_{n13}$ | $P_{n14}$ | | $P_{nk}$ |

FIG. 17

| SERVICES | | #1 | #2 | ... | #i | #(i+1) | #(i+2) | #(i+3) | ... | #p | #(p+1) | #(p+2) | ... | #n |
|---|---|---|---|---|---|---|---|---|---|---|---|---|---|---|
| S#1 (HEALTH CHECK) | | $P'_{11}$ | $P'_{12}$ | | - | - | - | - | | | | | | - |
| ... | | | | | | | | | | | | | | |
| S#i (NAVIGATION) | | - | - | | $P'_{ij}$ | $P'_{i(j+1)}$ | $P'_{i(j+2)}$ | - | | | | | | - |
| S#i+1 (IMAGE INFORMATION) | | - | - | | $P'_{1j}$ | $P'_{i(j+1)}$ | - | $P'_{(i+1)(j+3)}$ | | | | | | - |
| ... | | | | | | | | | | | | | | |
| S#m (WEB BROWSER) | | - | - | | - | - | - | | | $P'_{mp}$ | $P'_{m(p+1)}$ | $P'_{m(p+2)}$ | | - |
| ... | | | | | | | | | | | | | | |
| S#n | | $P'_{n1}$ | $P'_{n2}$ | | $P'_{nj}$ | $P'_{n(j+1)}$ | $P'_{n(j+2)}$ | - | | | | | | $P'_{nn}$ |

PARAMETERS FOR MODULES

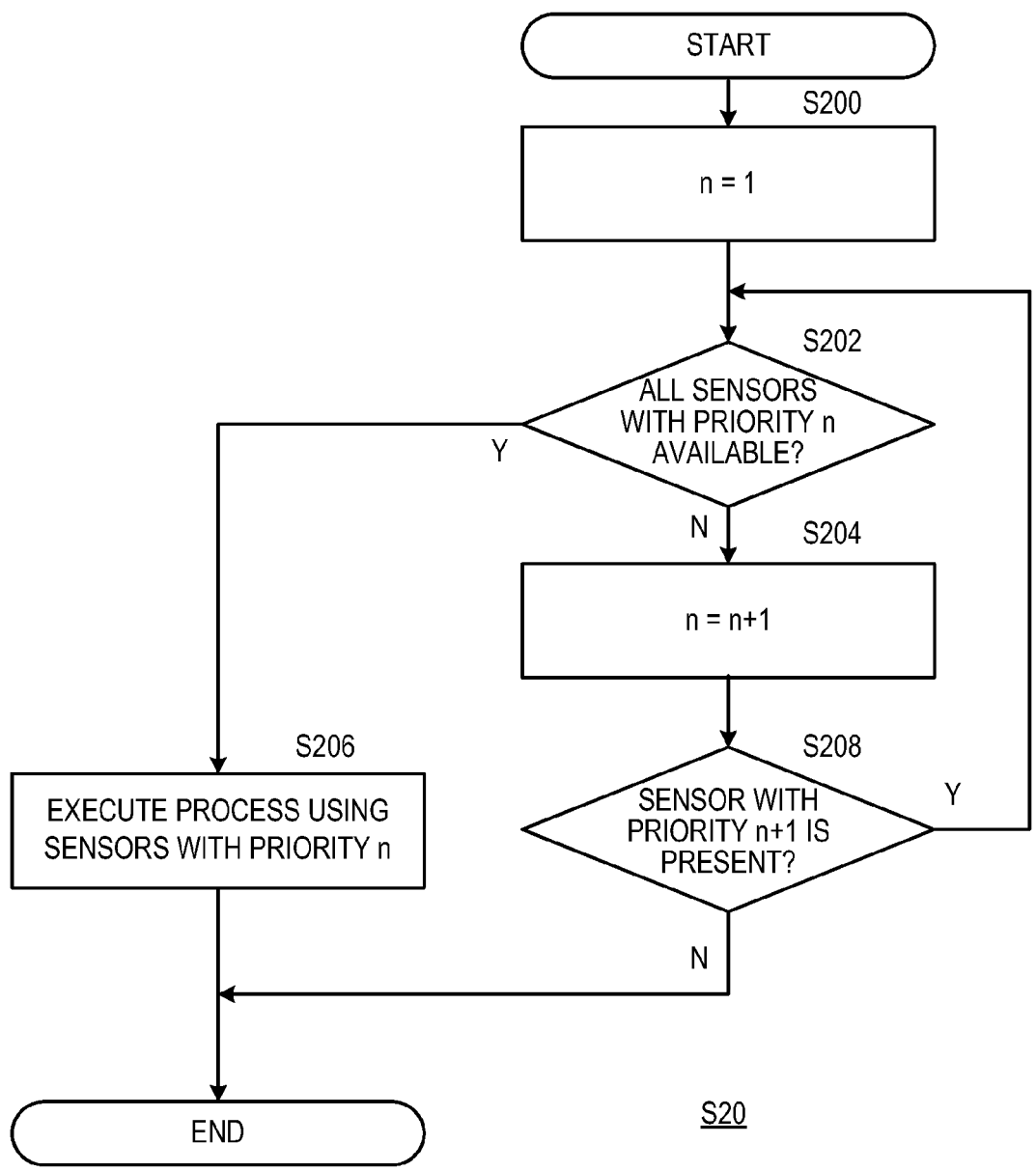

ns with a lower priority exist and until information service can be provided. Therefore, information services with various priorities of sensor combinations in order are retained in advance, and an information service corresponding to a combination of currently available sensors can be provided.-->

INFORMATION SERVICE PROVIDING SYSTEM, INFORMATION SERVICE PROVIDING DEVICE, AND METHOD THEREFOR

CROSS-REFERENCE TO RELATED APPLICATIONS

The present application is a U.S. national stage application claiming the benefit of International Application No. PCT/JP2009/054140, filed on Mar. 5, 2009, the entire contents of which is incorporated herein by reference in its entirety.

TECHNICAL FIELD

The present invention relates to an information service providing system, information service providing device, and a method therefor for adaptively using sensors thereby providing an information service.

BACKGROUND ART

For example, Non-Patent Documents 1 and 2 disclose an active meta-level system for dynamically interconnecting devices such as databases.

Non-Patent Document 1: Shuichi KURABAYASHI, Naoki ISHIBASHI, and Yaushi KIYOKI: "Active Multidatabase System for Mobile Computing Environment", Information Processing Society of Japan, The Special Interest Group Technical Reports of IPSJ, 2000-DBS-122, 2000, 463-470.

Non-Patent Document 2: Shuichi KURABAYASHI, Naoki ISHIBASHI, and Yasushi KIYOKI: A Multidatabase System Architecture for Integrating Heterogeneous Databases with Meta-Level Active Rule Primitives. In Proceedings of the 20th IASTED International Conference on Applied Informatics, 2002, 378-387.

DISCLOSURE

Means for Solving the Problems

The information service providing device of the disclosure of the present application comprises: one or more combinations to which a unique priority in each provision of information service is assigned and each of which is a combination of one or more sensor driving program modules which are used in each provision of an information service; one or more processing program modules for performing a process on external accepted content information; an input device for accepting external input specifying one or more of a plurality of information services; a selector for selecting a combination of sensor driving program modules contained in a first combination to which the highest priority is assigned and in which at least all sensors adapted to the sensor driving program modules contained in the combination are available and the one or more processing program modules, on the basis of associating information associating each of the plurality of information services, a combination of the one or more sensor driving program modules, which is needed for its implementation, and the one or more processing program modules; a plurality of kinds of sensors each of which at least adapted to one of the sensor driving program modules contained in a combination of the one or more sensor driving program modules; an execution device for responding to the specified information service, executing the set processing program modules and output program modules, executing sensor driving program modules contained in a combination to which the highest priority is assigned and in which at least all sensors adapted to the sensor driving program modules contained in the combination are available, and delivering information input-output between these so as to be adapted to the implementation of the specified information service, thereby implementing the specified information service; and an output device for outputting the result of the implemented one or more information services, and is configured in such a manner that a combination of the executed sensor driving program modules drives the adapted sensors, detects information according to the kind of this sensor, and outputs the information as the information of sensor, and each of the executed processing program modules processes the information of sensor, which is input from the sensor driven by the executed sensor driving program and the provided content information, and outputs a processing result.

SUMMARY

Here, the summary of the disclosure of the present application will be described.

However, note that, the description here is intended to help the understanding of the disclosure of the present application only and not intended to limit the technical scope.

The information service providing device of the disclosure of the present application is configured so as to detect the context (situation) of a user by combining different types of sensor functions in hybrid, and is called, for example, a hybrid sensing system.

The information service providing device of the disclosure of the present application comprises a pulse sensor, perspiration sensor, brain wave sensor, viewpoint detection sensor, and the like, which are sensors capable of obtaining physical information such as the pulse, perspiration, brain wave, and viewpoint of a user, and the like.

For example, as an information service, in order to determine which component part of Web content a user takes an interest in, a component the user is viewing can be determined by sight line detection sensor, and the degree of his/her interest can be determined quantitatively from the information obtained from the other sensor.

Therefore, for the implementation of such information service, all of the pulse sensor, perspiration sensor, brain wave sensor, and viewpoint detection sensor are preferably used as the combination of sensor.

However, when it is intended to provide such information service, there may be a case where the brain wave sensor and viewpoint detection sensor are not provided in a service providing device.

Even in such cases, by processing component contained in displayed Web content and information obtained from the pulse sensor and perspiration sensor, a component which the user admires can be deduced and the degree of his/her interest can be determined.

Thus, by determining in advance a combination of sensors used for the provision of an information service and its priority, and using the sensors contained in a combination with a lower priority when any of the sensors contained in a combination with a higher priority is not available, an information service with a quality pursuant to a case, in which sensors of a combination with a higher priority are used, can be provided.

In addition, the information service providing device of the disclosure of the present application provides a high-quality information service if at all possible with the use of a combination of sensor in order of higher priority upon receipt of a designation of a user desired information service, and is configured in such a manner that when a combination of sensor is not available in order of higher priority, an information service with a quality pursuant to an information service for which a combination of sensor is used in order of higher priority, can be provided by using a sensor with a lower priority.

The technical advantages of the disclosure of the present application and other technical advantages will be apparent to a person skilled in the art by reading the detailed description of the embodiments illustrated in the drawings.

The accompanying drawings are hereby incorporated into the description of the present application as a part thereof, illustrate the embodiments of the disclosure of the present application, and together with the description, fulfill a role in illustrating the principle of the disclosure of the present application.

It should be understood that the drawings referred to in the description of the present application are, if not otherwise specified, not drawn to scale.

BRIEF DESCRIPTION OF THE DRAWINGS

The embodiments of the disclosure of the present application will be best understood, on its configuration and operation, with reference to the following description with drawings.

FIG. 6 is a first diagram illustrating a first table of service definition stored in the input analyzing DB shown in FIG. 4;

FIG. 7 is a first diagram illustrating a table of service execution parameters, which is stored in the parameter DB shown in FIG. 4;

FIG. 8 is a first diagram illustrating a table of sensor parameters, which is stored in the parameter DB shown in FIG. 4;

FIG. 15 is a second diagram illustrating a table of service definition, which is stored in the input analyzing DB shown in FIG. 4;

FIG. 16 is a second diagram illustrating the table of sensor parameters, which is stored in the parameter DB shown in FIG. 4;

FIG. 17 is a second diagram illustrating the table of service execution parameters, which is stored in the parameter DB shown in FIG. 4;

FIG. 20 is a flow chart illustrating the operation (S20) of the terminal program (FIG. 4) in a case where three or more combinations of sensors are present for the implementation of an information service.

DETAILED DESCRIPTION

[First Embodiment]

Hereinafter, the first embodiment of the disclosure of the present application will be described in detail.

The embodiment of the disclosure of the present application is illustrated in the accompanying drawings.

Although the disclosure of the present application will be described in relation to the embodiment, it will be understood by a person skilled in the art that this embodiment is not intended to limit the disclosure of the present application to the disclosure.

On the contrary, the disclosure of the present application is intended to include alternatives, changes and equivalents, which may be included in the spirit of the disclosure of the present application and the claims of the present application.

In addition, the disclosure of the present application will be described specifically and in detail so that the disclosure of the present application becomes sufficiently understandable.

However, as it will be apparent to a person skilled in the art, the disclosure of the present application may be implemented even if not using all of these matters described specifically and in detail herein.

In addition, a well-known technique, procedure, component and circuit may not be described in detail so as not to obscure the aspects of this disclosure unnecessarily.

However, it should be noted that these and all of the similar words and terms should be associated with appropriate physical quantities, and are merely convenient labels assigned to these quantities.

As it will be apparent from the following discussions, if not otherwise specified, throughout the disclosure of the present application, it is understood that the discussion, in which words such as "receive", "deliver", and "set" are used, indicates the action and process of a computer system such as an electronic computing device.

A computer system such as an electronic computing device handles the data represented as a register of a computer system and a physical (electronic) quantity in a memory, and converts them into the other data represented similarly as a physical quantity in a computer system memory, register or the other of the kind: an information storage, transmission, or display device.

In addition, the disclosure of the present application is also suitable for the use of, for example, other computer systems such as an optic and mechanical computer.

[Information Service Providing System 1]

Hereinafter, an information service providing system 1 to which the disclosure of the present application is applicable will be described.

Figure 1:
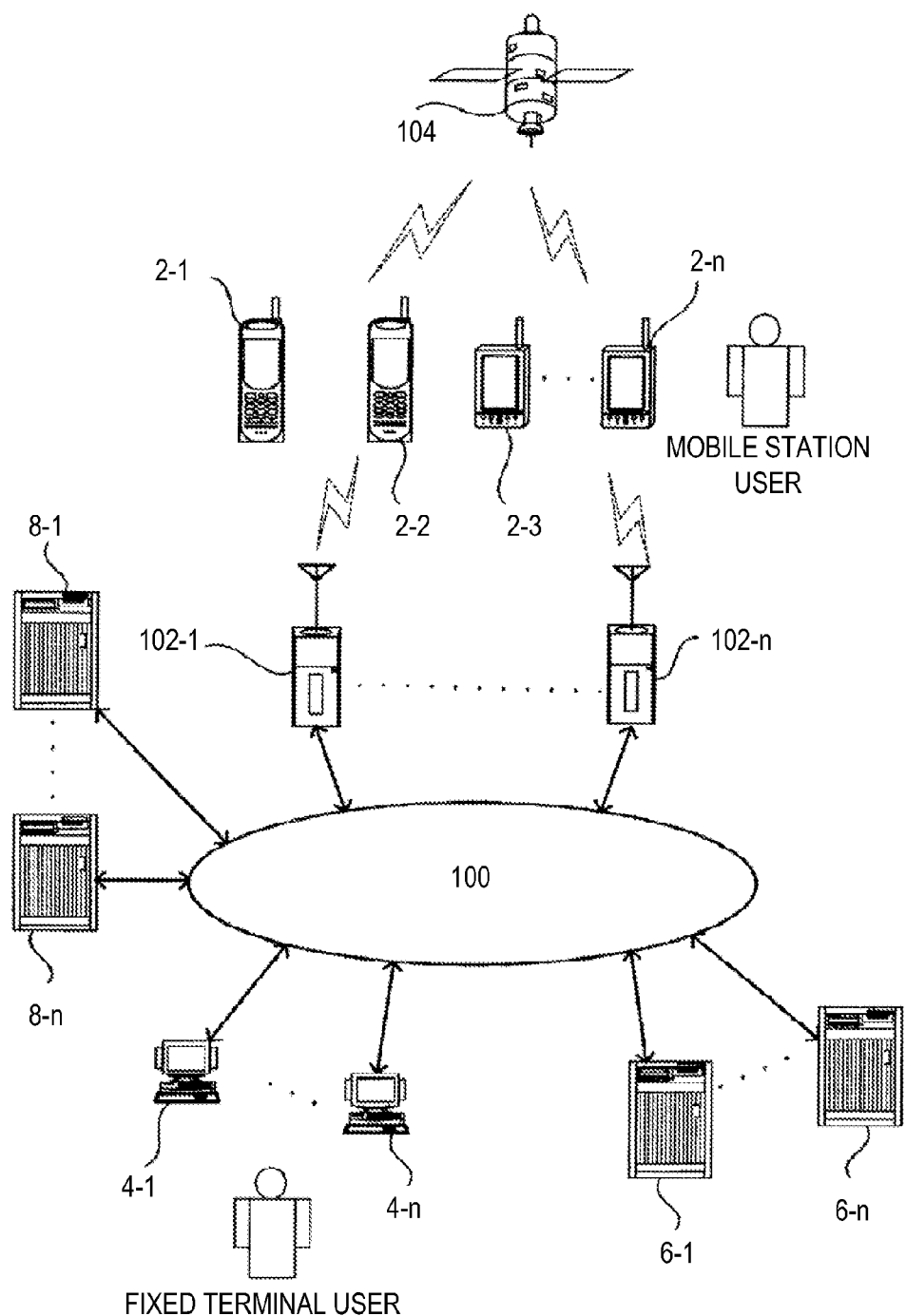
FIG. 1 is a diagram illustrating the configuration of an information service providing system to which the disclosure of the present application is applicable.

FIG. 1 is a diagram illustrating the configuration of an information service providing system 1 to which the disclosure of the present application is applicable.

The information service providing system 1 is configured such that mobile stations 2-1 to 2-$n$, fixed terminals 4-1 to 4-$n$, base stations 102-1 to 102-$n$, module-parameter server devices 6-1 to 6-1 and Web servers 8-1 to 8-$n$ are connected through a network 100 accommodated to both wired and wireless communications.

In addition, the mobile stations 2-1 to 2-$n$ may receive a radio signal for position detection from a GPS artificial satellite 104 in a location suitable for receiving radio waves, such as in the open air.

In the information service providing system 1, the mobile stations 2-1 to 2-$n$ are, for example, a mobile telephone, PDA (Personal Digital Assistant) capable of wireless communication, a digital camera and a luggable personal computer.

The fixed terminals 4-1 to 4-$n$ are, for example, a desktop computer.

In addition, the base stations 102-1 to 102-$n$ perform the transmission of data between the fixed terminals 4-1 to 4-$n$ and the mobile stations 2-1 to 2-$n$ through a wireless line.

Web servers 8-1 to 8-$n$ return Web data upon request from the mobile station 2 and fixed terminal 4.

In addition, mobile stations 2-1 to 2-$n$ may receive a radio signal for position detection from a GPS artificial satellite 104 in a location suitable for receiving radio waves, such as in the open air.

In addition, n indicates an integer which is 1 and above, and i, j indicate integers which satisfy 1≦i, j≦n; however, each of these symbols i, j and n is not limited to indicate the same number at all times.

In addition, hereinafter, in a case where any one or more of a plurality of component parts are indicated without specifying mobile stations 2-1 to 2-$n$ and the like may be simply abbreviated as the mobile station 2.

In addition, component parts which can be the main constituent of information communication and information processing such as the base station 102, mobile station 2, fixed terminal 4 and module-parameter server device 6 may be generically referred to as a node.

In addition, hereinafter, if not otherwise specified, in each figure, the same reference sign is assigned to substantially the same component part and process.

The information service providing system 1 implements information processing by nodes and information communication between nodes by these component parts, and moreover, functions as the abovementioned hybrid sensing system.

[Hardware Configuration]

Hereinafter, the hardware configuration for each node of the information service providing system 1 will be described.

Figure 2:
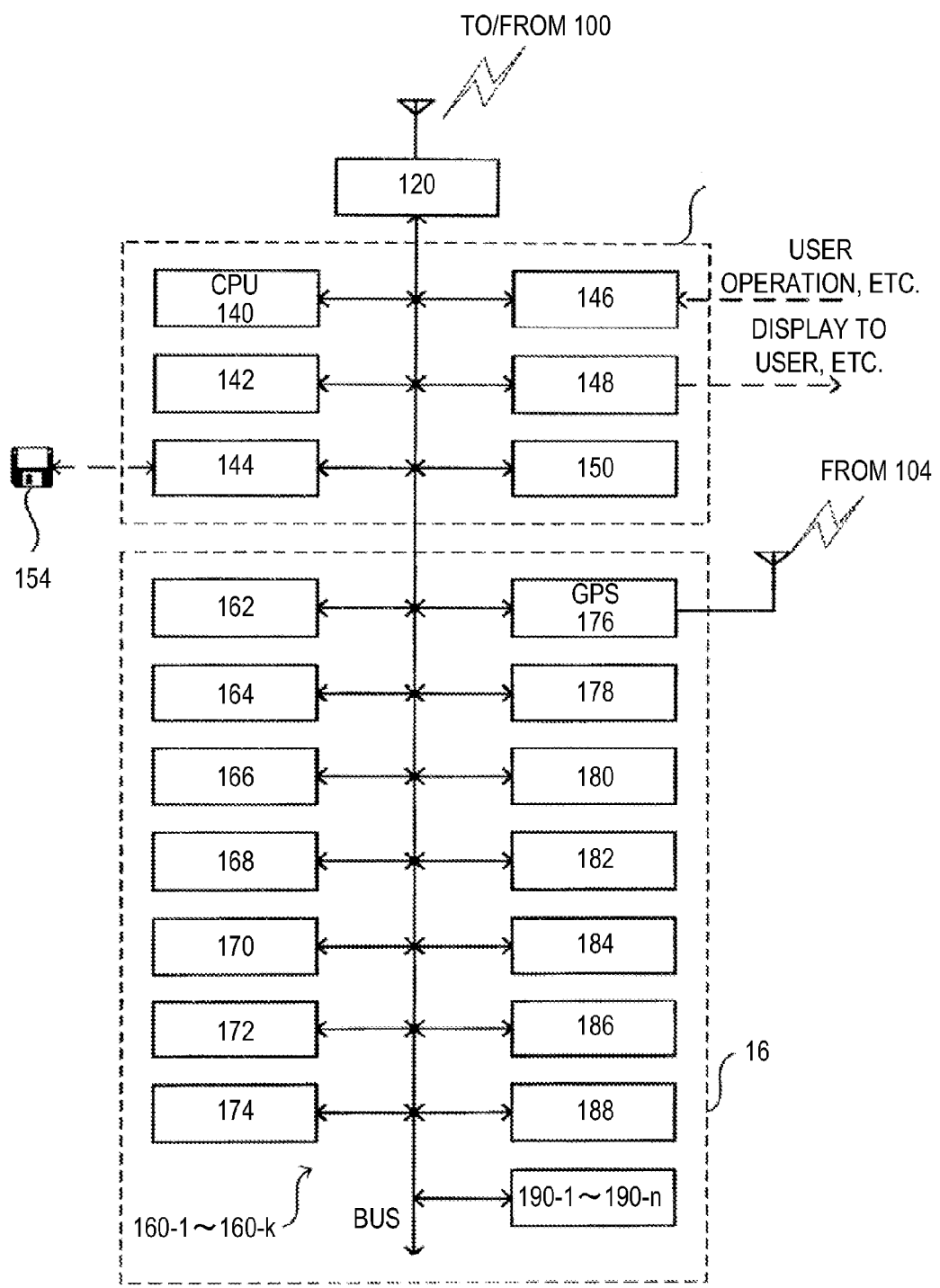
FIG. 2 is a diagram illustrating the hardware configuration of the mobile station and fixed terminal shown in FIG. 1.

FIG. 2 is a diagram illustrating the hardware configuration of the mobile station 2 and fixed terminal 4 shown in FIG. 1.

As illustrated in FIG. 2, the mobile station 2 and fixed terminal 4 is configured such that communication device 120 which is connected to a network 100 through a wireless communication line or a wired communication line, a data processing unit 14 and a sensor unit 16 are connected through a bus (BUS).

The data processing unit 14 includes a CPU 140, a memory 142, interrupt control device, timer device, a CPU peripheral device 144 such as a recording medium interface for performing read and write of data to a recording medium 154, an input button such as a numeric keypad, input device 146 such as a microphone, an output device 148 such as a liquid crystal display device and a speaker, a camera 150 in which a dynamic image and a static image can be taken and taken images are output as digital-format image data, and the like.

The sensor unit 16 comprises, for example, a perspiration sensor 162, a pulse sensor 164, a blood pressure sensor 166, a brain wave sensor 168, a cardiac signal sensor 170, a body temperature sensor 172, a blood component sensor 174, a GPS 176, a direction sensor 178, an accelerated velocity sensor 180, a speed sensor 182, a temperature-humidity sensor 184, an viewpoint detection sensor 186, a pedometer 188 and other sensors 190-1 to 190-$n$ such as sensors for using a RF-ID sensor (hereinafter, these will be generically referred to as sensors 160-1 to 160-$k$ (k is the number of the sensors that a sensor unit 16 contains)).

Thus, the mobile station 2 and fixed terminal 4 have component parts as in a common computer in which information detection by sensor, information processing and information communication can be performed.

In addition, in FIG. 2, a case where the sensor unit 16 includes each of the multiple kinds of sensors 160 is shown as an illustrative embodiment; however, the sensor unit 16 may include multiple sets of the multiple kinds of sensors 160.

In addition, each of the abovementioned sensors contained in the sensor unit 16 is driven and controlled by an adapted device driver program, and detects information corresponding to each kind and output as the information of sensor.

In the sensor unit 16, the perspiration sensor 162 detects the amount of perspiration of a user (Mobile Station User, Fixed Terminal User) of the mobile station 2 and fixed terminal 4.

The pulse sensor 164 detects the pulse of a user of the mobile station 2 or the like.

The blood pressure sensor 166 detects the blood pressure of a user of the mobile station 2 or the like.

The brain wave sensor 168 detects the brain wave of a user of the mobile station 2 or the like.

The cardiac signal sensor 170 detects the electronic signals generated by the heart of a user of the mobile station 2 or the like.

The body temperature sensor 172 detects the body temperature of a user of the mobile station 2 or the like.

The blood component sensor 174 detects the amount of blood component such as blood glucose, the levels of neutral fat in blood, the level of uric acid in blood.

The GPS 176 detects the location (latitude/longitude) of the mobile station 2 or the like using the radio signal from the GPS artificial satellite 104 (FIG. 1).

The direction sensor 178 detects the moving direction of mobile station 2 or the like by compass, gyrocompass and the like.

The accelerated velocity sensor 180 detects the accelerated velocity given to the mobile station 2 or the like.

The speed sensor 182 detects the mobile speed of mobile station 2 or the like.

The temperature-humidity sensor 184 detects the temperature/humidity of open air.

The viewpoint detection sensor 186 photographs the face of a user of the mobile station 2 or the like and detects the viewpoint of the user.

The pedometer 188 detects the number of steps of a user of the mobile station 2 or the like.

Figure 3:
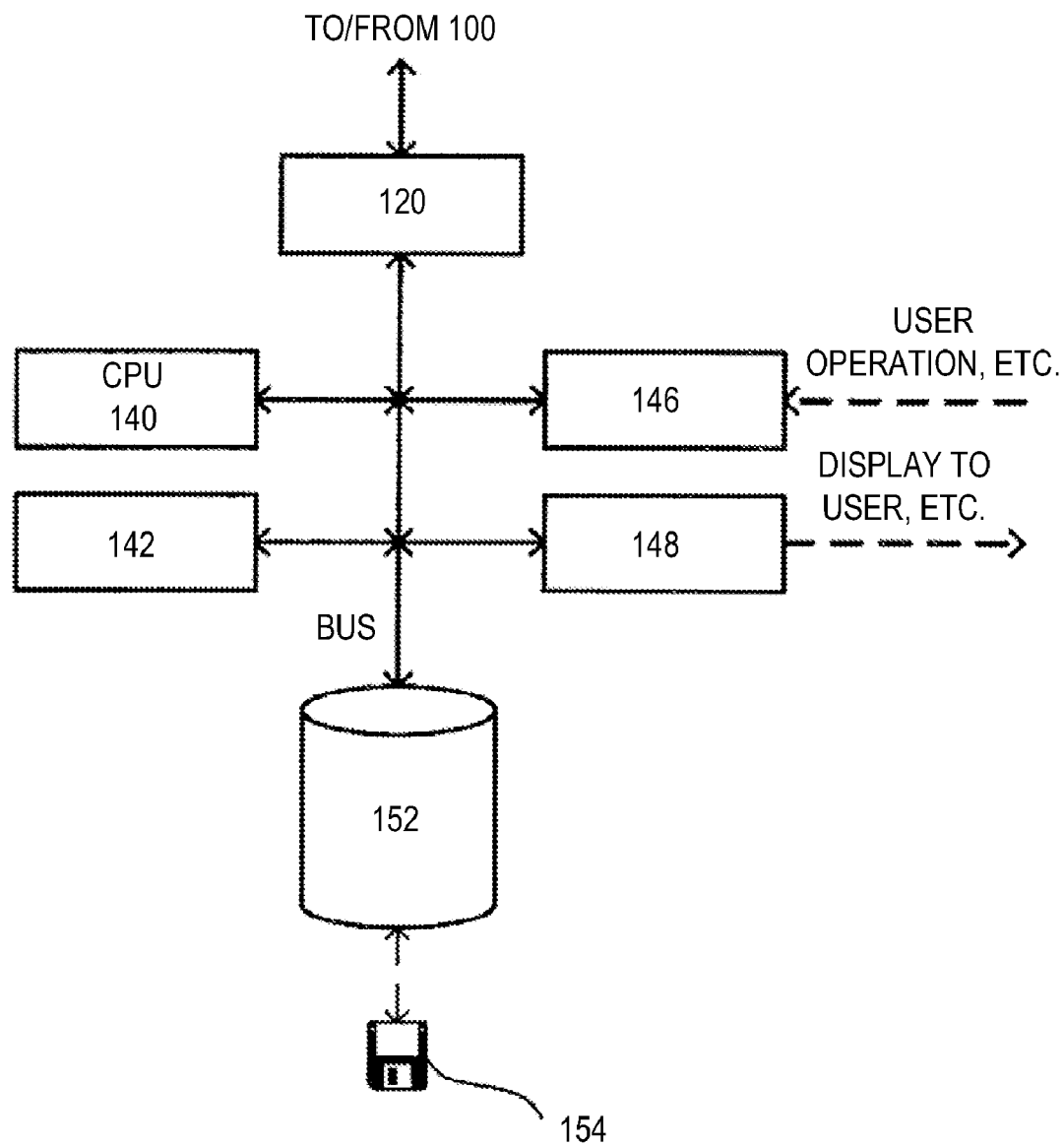
FIG. 3 is a diagram showing the hardware configuration of the server device shown in FIG. 1.

FIG. 3 is a diagram showing the hardware configuration of the module-parameter server device 6 shown in FIG. 1.

As illustrated in FIG. 3, module-parameter server device 6 includes a communication device 120, a CPU 140, a memory 142, a CPU peripheral device 144, an input device 146, an output device 148, a recording device 152 such as a HDD/CD device, and the like.

Thus, the module-parameter server device 6 has component parts as in a common computer in which information processing and information communication are enabled.

[Software]

Hereinafter, software (program) performed in each node of the information service providing system 1 will be described.

[Terminal Program 20]

Firstly, a terminal program 20 performed in the mobile station 2 and fixed terminal 4 will be described.

Figure 4:
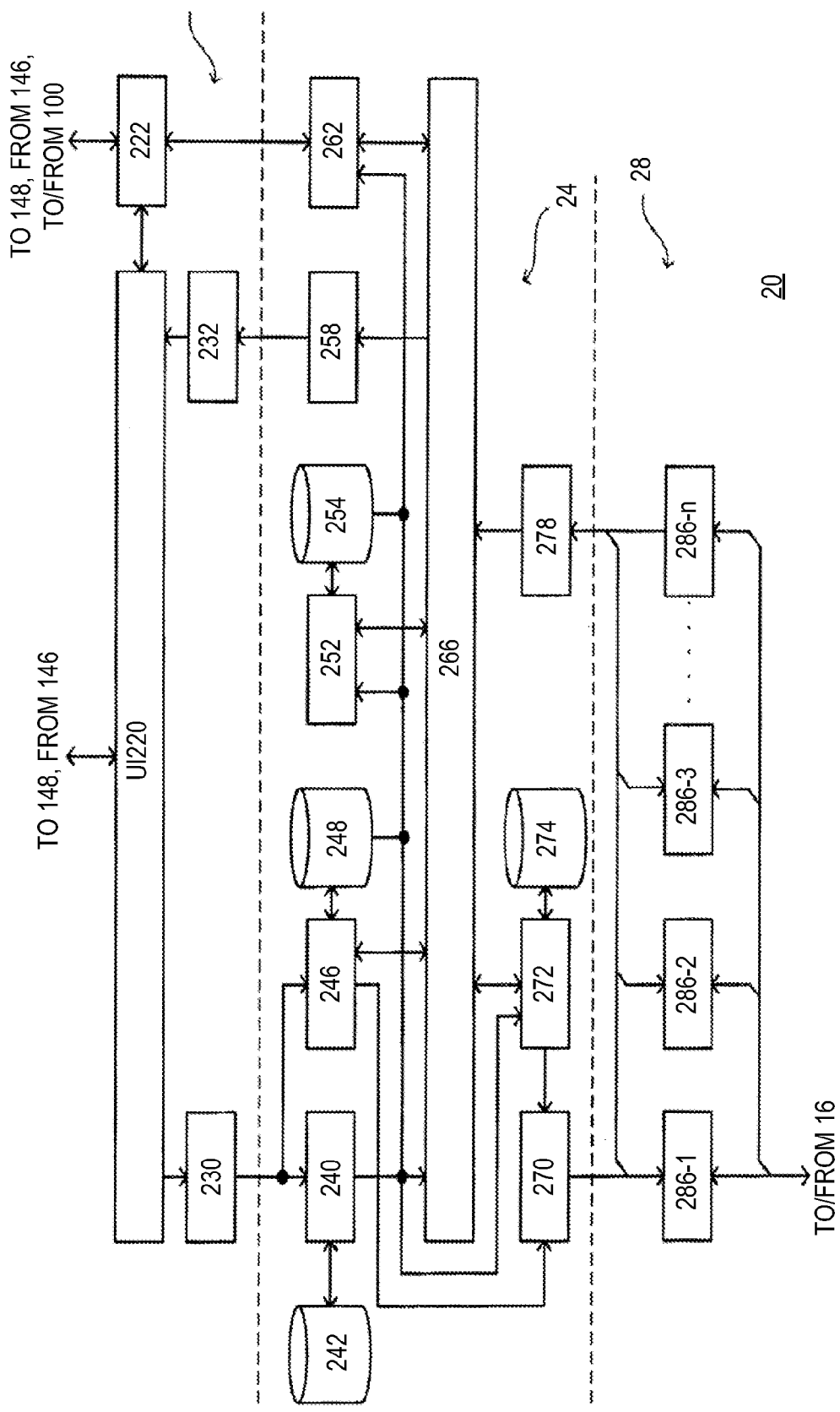
FIG. 4 is a diagram showing a terminal program executed in the mobile station and fixed terminal shown in FIG. 1, FIG. 2.

FIG. 4 is a diagram showing a terminal program 20 performed in the mobile station 2 and fixed terminal 4 shown in FIG. 1, FIG. 2.

As illustrated in FIG. 4, the terminal program 20 includes a service providing unit 22, a middleware 24 and a sensor driving unit 28.

The service providing unit 22 includes a user interface unit (UI) 220, a communication processing unit 222, an application input unit 230 and an information output unit 232.

The middleware 24 includes an input analyzing unit 240, an input analyzing database (DB) 242, a parameter setting unit 246, a parameter DB 248, a module selection unit 252, a module DB 254, an information creating unit 258, an information acquiring unit 262, a module execution control unit 266, a sensor control unit 270, a sensor selection unit 272, a sensor drive module DB 274 and a sensor output processing unit 278.

The sensor driving unit 28 includes sensor drive modules 286-1 to 286-$k$.

The terminal program 20 is loaded into the memory 142 of the mobile station 2 and fixed terminal 4 through a recording medium 154 (FIG. 2, FIG. 3), a network 100 and the like, and executed on an OS (not shown) executed in the mobile station 2 and fixed terminal using specifically the hardware resources of the mobile station 2 and fixed terminal 4 (same in the following programs and modules).

The terminal program 20 receives the designation of a user-desired information service by these component parts, selects a sensor 160, a sensor drive module 286, a service execution module 300 and an information creation module 310 (described later with reference to FIG. 5) that are needed for the implementation of the specified information service, and implements the specified information service by combining these.

In addition, when a plurality of information services are specified, the terminal program 20 implements these plurality of information services simultaneously.

[Service Providing Unit 22]

In the service providing unit 22 of the terminal program 20, a UI 220 displays to the display device of the output device 148, for example, a GUI (Graphic User Interface) image (not shown) for prompting a user to select an information service.

In addition, the UI 220 accepts a user's operation for specifying a desired information service according to the displayed GUI image from the input device 146, and outputs the information for specifying the specified information service to the application input unit 230.

Furthermore, the UI 220 outputs the audio signal which is input from the microphone of the input device 146 to the communication processing unit 222, and outputs the audio signal input from the communication processing unit 222 to the speaker of the output device 148.

The communication processing unit 222 performs the process for the audio transmission in the mobile station 2 and fixed terminal 4 and common information communication, and the process for the information communication with the module-parameter server device 6 through the network 100.

The application input unit 230 accepts the information specifying the information service input from the UI 220 and outputs to the middleware 24.

The information output unit 232 accepts the result of the specified information service from the middleware 24, and outputs image, audio, and the like to each of the specified services in a predetermined format through the UI 220.

[Sensor Drive Module, Service Execution Module, Information Creation Module]

To help the understanding of the middleware 24, before the description of the middleware 24, sensor drive module 286, service execution module 300 and information creation module 310 (these are generically referred to as modules) will be described.

Figure 5:
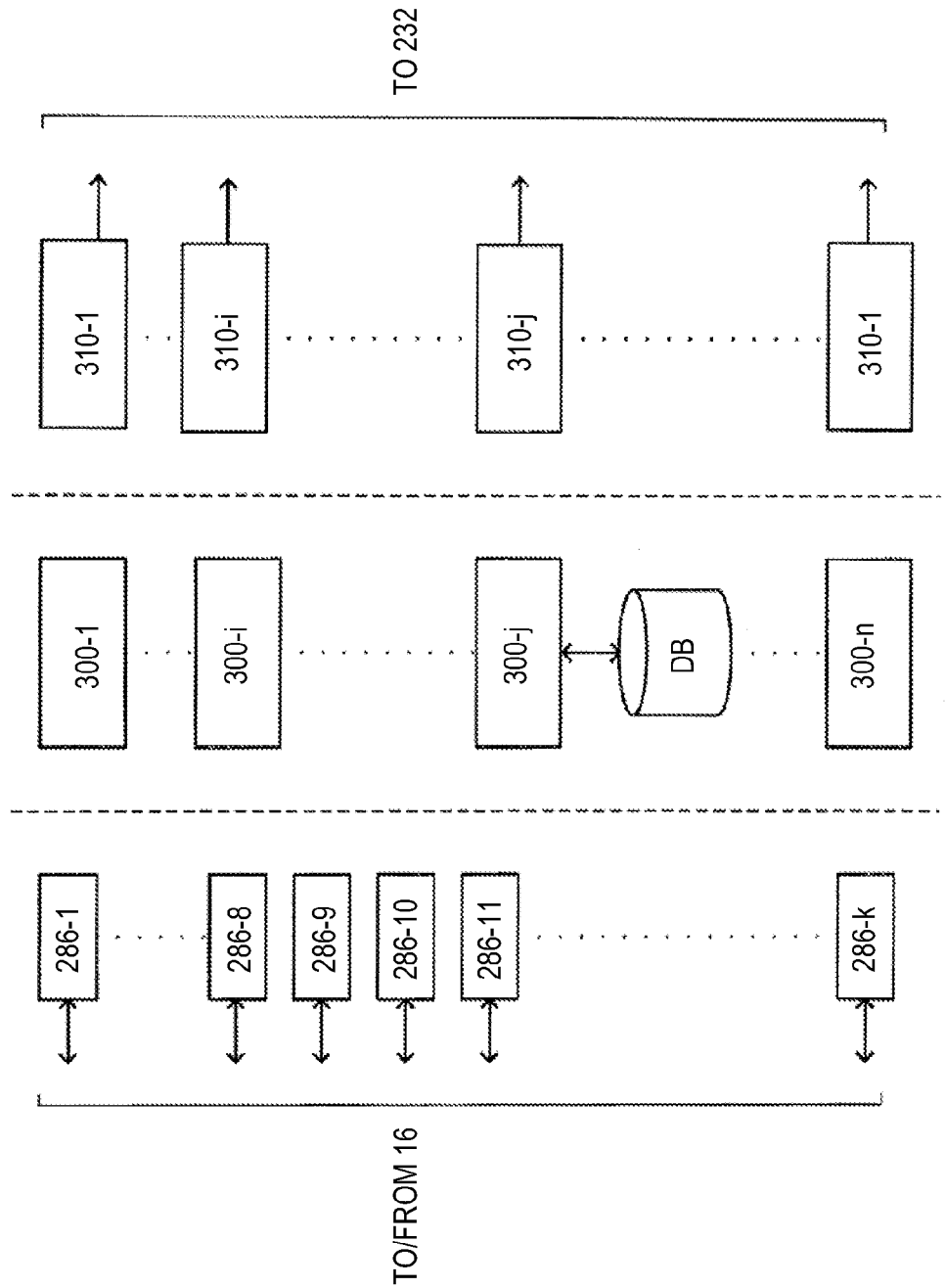
FIG. 5 is a diagram showing a sensor drive module, a service execution module and an information creation module executed by the terminal program shown in FIG. 4.

FIG. 5 is a diagram showing a sensor drive module 286, a service execution module 300 and an information creation module 310 executed by the terminal program 20 shown in FIG. 4.

These modules are executed by the control of the middleware 24.

Each of the sensor drive modules 286-1 to 286-$k$ correspond to each of the sensors 160-1 to 160-$k$, and adapts to the corresponding sensor 160.

That is, the sensor drive module 286 corresponding to sensor 160 selected for the implementation of an information service specified by a user receives the setting of the sensor parameters (P; described later with reference to FIG. 8) for optimally operating the corresponding sensor 160 and operates the sensor 160 using the set sensor parameters, P.

The sensor drive module 286 further creates the information of sensor, which indicates the information such as temperature/location (latitude/longitude) detected by the corresponding sensor 160 and outputs to the service execution module 300 selected for the implementation of the information service specified by the user.

The selected service execution module 300 receives the setting of service execution parameters (P'; described later with reference to FIG. 7) which are for optimally executing the selected process.

In addition, the service execution module 300 receives the information of sensor from the sensor drive module 286 corresponding to selected one or more sensors 160 and process the received information of sensor using the set service execution parameters P' thereby executing a specified information service.

The selected service execution module 300 outputs the processing result of an information service to the information creation module 310 selected for the implementation of the information service specified by a user.

The selected information creation module 310 receives the setting of information creation parameters P' (for example, the output format of the result of an information processing service) which are for optimally executing the selected process.

In addition, information creation module 310 receives the processing result from selected one or more service execution modules 300 and processes the received processing result of sensor using the set information creation parameters P' thereby creating the result of an information processing service in accordance with a predetermined format (audio, image, image format, etc.) for each of the information processing services and outputs to the information output unit 232 of the service providing unit 22.

[Middleware 24/Sensor Driving Unit 28]

FIG. 6 is a first diagram illustrating a first table of service definition stored in the input analyzing DB 242 shown in FIG. 4.

In the middleware 24, the input analyzing DB 242 stores the table of service definition shown in FIG. 6 in such a way that the input analyzing unit 240 can reference thereto.

The input analyzing unit 240 references to the table of service definition stored in the input analyzing DB 242 and notifies a module corresponding to a specified information service to the module execution control unit 266, module selection unit 252, information acquiring unit 262 and the sensor selection unit 272.

The information acquiring unit 262 references to the parameter DB 248 and module DB 254 and in the notification from the input analyzing unit 240, and, within the specified information services, determines if there are modules, sensor parameters P, service execution parameters P' and information creation parameters P' (these are generically referred to as modules and parameters) which are needed for the implementation of an information service that is determined to be implementable by the module execution control unit 266.

When any one or more of the modules and parameters needed for the implementation of a specified information service are not present, the information acquiring unit 262 requests one or more of the modules and parameters that are not present in the mobile station 2 and fixed terminal 4 to the module-parameter server device 6 (FIG. 1) through the network 100.

The information acquiring unit 262 stores one or more of the modules returned from the module-parameter server device 6 in the module DB 254 in response to this request, and also stores any one or more of the sensor parameters, P, service execution parameters P' and information creation parameters P'(these are generically referred to as parameters) that are returned from the module-parameter server device 6 in the parameter DB 248.

In addition, in the combinations of one or more service execution modules 300 and one or more information creation modules 310 (MS#1-MS#n) that are used in each information service, the information for defining that which information of sensor from a sensor 160 (sensor drive module 286) the service execution module 300 would accept is contained.

In addition, in this combination (MS#1-MS#n), the information for defining that, with which one of the other service execution modules 300 a service execution module 300 would perform the input and output of what information, and which service execution module 300 would output a processing result to which of the information creation modules 310, is contained.

In addition, in this combination (MS#1-MS#n), the information for defining that, with which one of the other information creation module 310 an information creation module 310 would perform the input and output of what information, and which information creation module 310 would output a conclusive result of an information service to the information creating unit 258, is indicated.

The priority of the sensor 160 indicates that which sensor 160 (sensor drive module 286) should be used when a plurality of sensors 160 are available in one specified information service.

In addition, as described above, FIG. 6 illustrates that, in a case where the mobile station 2 and fixed terminal 4 provide a navigation service as an information service, when GPS 176 (FIG. 2) can receive the radio signal from the GPS artificial satellite 104 (FIG. 1), the service execution module 300 should process the information of sensor (latitude/longitude) of the GPS 176, and when the GPS 176 cannot receive the radio signal, the service execution module 300 should compute the position information by the integral treatment using the information of sensor, which is output by the direction sensor 178, information service providing system 180 and the accelerated velocity sensor 182.

The priority of information services is indicated by the numbers such as 1, 2, 3 . . . , for example, as is the case with the priority of the sensor 160, and indicates that the smaller the number, the higher the priority.

The priority of information services indicates which information service should be given a priority and executed, for example when a plurality of information services are specified, in a case where not all services can be executed because a plurality of information services need the same resource, or due to the limit of processing capacity of the data processing unit 14 (FIG. 2) of the mobile station 2 and fixed terminal 4.

Thus, for example, when not all of a plurality of information services using the same sensor 160 can be executed, only the information service with the highest priority is executed.

In addition, when not all of a plurality of information services can be executed due to the limit of processing capacity of the data processing unit 14, an information service is executed from a service with a higher priority in the order and an information service with a lower priority, which makes the processing capacity of the data processing unit 14 reach the limit when executed, is not executed.

In addition, the priority of information services indicates a combination of which sensors 160 should be given a priority and executed, for example, when an information service is specified and a sensor which can provide the sensor data needed to improve the accuracy, speed of response, and degree of detail or the like of the information service is not available.

For example, the priority of information services indicates that in a health check service, when one blood pressure sensor 166, one pulse sensor 164 and two brain wave sensors 169 are available, the best result can be obtained, whereas when only one blood pressure sensor 166 and pulse sensor 164 is available, the execution of this health check service is possible by using these two sensors 160.

FIG. 7 is a first diagram illustrating a table of parameters for modules, which is stored in the parameter DB 248 shown in FIG. 4.

FIG. 8 is a first diagram illustrating a table of sensor parameters, which is stored in the parameter DB 248 shown in FIG. 4.

The parameter DB 248 stores the table of parameters for modules shown in FIG. 7, the table of sensor parameters shown in FIG. 8 and the table of information creation parameters, the composition of which is similar to the table of parameters for modules shown in FIG. 7 in such a way that the stored table can be referenced from the parameter setting unit 246 and information acquiring unit 262.

The parameter setting unit 246 references the table of sensor parameters, table of parameters for modules and table of information creation parameters that are stored in the parameter DB 248, and outputs the sensor parameters, P of the sensor 160 (sensor drive module 286) needed for the implementation of only the information service that is determined to be implementable within the specified services by the module execution control unit 266 to the sensor control unit 270.

In addition, parameter setting unit 246 outputs the service execution parameters P' and information creation parameters P' of the service execution module 300 and information creation module 310 needed for the implementation of a specified service to the module execution control unit 266.

Hereinafter, the role of the table of service definition and table of sensor parameters shown in FIG. 7 and FIG. 8 will be described.

For the implementation of the abovementioned hybrid sensing system, the table of service definition and table of sensor parameters are used to describe the patterns of the combination of different types of the sensors 160 for user's purpose.

First, the table of service definition (FIG. 7) will be described.

The correspondence between an extraction object context and the combination of sensors 160 is set in the table of service definition.

The setting value for the table of service definition indicates the number of sensors to be used, and numeric value 0 indicates that a sensor 160 to which this numeric value is assigned would not be used.

In addition, a plurality of different information services may be described in the table of service definition.

Furthermore, in the table of service definition (FIG. 7), the priority corresponding to the combination of sensors 160 is set to the same information services.

The priority is, for example, represented by numeric values 0, 1, 2, 3 . . . , and the combination of sensors 160 to which a small numeric value is set is used on a priority basis.

The priority of the sensor 160 corresponding to this information service is, for example, when an information service is specified, a combination of which sensors 160 should be given a priority and used according to the case where all of the sensors 160 needed to improve the accuracy, speed of response, degree of detail, and the like of the information service are available, and the case where only a part of the sensors is available.

Here, in an information service for providing health information, an illustrative embodiment is given, wherein when the brain wave sensor 168 (high-precision, 3), blood pressure sensor 166 (high-precision, 1), pulse sensor 164 (high-precision, 1) and the body temperature sensor 172 (high-precision, 1) are used, the best result can be obtained, and the combination of these sensors 160 is set to the table of service definition along with a priority.

However, it is assumed that there is a case where the sensor 160 contained in the above-mentioned combination by which the best result can be obtained is not available due to the configuration and environment of a mobile terminal 2.

In such a case, the brain wave sensor 168 (high-precision, 1), pulse sensor 164 (middle-precision, 1) and body temperature sensor 172 (low-precision, 1) are set to the table of service definition along with a priority as the combination of sensors 160 by which the second-best result can be obtained.

As stated above, by setting a plurality of the combination of sensors 160 to the same information services, in a mobile station 2, even when the combination of sensors 160 by which the best result can be obtained is not available, an information service desired by the user of the mobile station 2 can be implemented with the combination of sensors 160 by which the second-best result can be obtained.

Next, the table of sensor parameters (FIG. 8) will be described.

In addition, for the implementation of the abovementioned hybrid sensing system, the table of sensor parameters is set for every sensor 160 in order for the selected sensor 160 to operate optimally.

In the table of sensor parameters, the sensor parameters appropriate for the extraction object context are set with numeric values.

For example, when a video camcorder is used as a sensor 160, the time between measurements S (second) and the image of resolving power p and the like are set to table of parameters as the sensor parameters.

A hybrid sensing system obtains the sensor data for implementation of an information service by referencing to the table of service definition and table of sensor parameters thereby the combination of the sensors available in each of the mobile stations 2 is adaptively selected for the situation and the parameter indicating an optimal operation is set to each of the selected sensors 160.

The procedure for the implementation of the hybrid sensing system will be described below.

Step 1-1: The user of the mobile station 2 specifies an information service.

Step 1-2: The table of service definition is referenced, and the combination of sensors 160 with a priority n (the default value of n=1) is selected in the specified information service.

Step 1-3: All sensors 160 contained in the combination of the sensors 160 selected in Step 2 are determined if they are available, and when only a part of this combination can be used, the process of the Step 2 is performed again and the combination of sensors 160 with a priority (n+1) is selected.

Step 1-4: For each of the sensors 160 selected by the process of Step 3, in the reference of the table of sensor parameters, parameters for optimally operating each of the selected sensors 160 are obtained.

Step 1-5: The sensor parameters obtained by the process of Step 4 are set to the corresponding sensors 160.

For example, in a health information service, a case where, in the table of service definition, the combination of one blood pressure sensor 166, one pulse sensor 164 and one body temperature sensor 172 is set to be priority 1, and the combination of one pulse sensor 164 and one body temperature sensor 172 is set to be priority 2, will be considered.

In this case, in a mobile station 2, if only the combination of one pulse sensor 164 and one body temperature sensor 172 is available, in a hybrid sensing system, the combination with a priority 2 of one pulse sensor 164 and one body temperature sensor 172 is selected, and further, the sensor parameters corresponding to each of the pulse sensor 164 and body temperature sensor 172, which are obtained by referencing to the table of sensor parameters are set to each of the pulse sensor 164 and body temperature sensor 172.

Furthermore, in a hybrid sensing system, the sensor data obtained from each of the sensor 160 is processed and an information service specified by the user of the mobile station 2 is provided by the procedure shown below.

Step 2-1: Sensor 160 accepts the sensor data needed for the implementation of the function for the provision of an information service.

Step 2-2: The process needed for the implementation of the function for the provision of an information service is performed using the sensor data accepted by the process of Step 1.

Step 2-3: On the basis of the processing result of Step 2-2, the information obtained as the result of the information service specified by the user (sound, character, image, moving picture, etc.) is displayed to the user through the display device and speaker of the mobile station 2, or the large screen monitor of a commercial space, and the like.

Hereinafter, the composition of the table of sensor parameters, table of parameters for modules and table of information creation parameters will be further described.

As illustrated in FIG. 8, in the table of sensor parameters, the information services (Services) which can be provided by the mobile station 2 and fixed terminal 4 and the sensor parameters, P (Sensor parameters) set to the sensor 160 (sensor drive module 286) in each of these information services and used to operate the sensor are associated with each other and stored.

The sensor parameters, P is used, for example as stated above, to adjust the sensitivity or the like of the perspiration sensor 164, blood pressure sensor 166 and body temperature sensor 172 when a health check is provided as an information service.

In addition, when a plurality of parameters is set to one sensor 160, the sensor parameters, P are used to adjust a plurality of settings corresponding to one sensor 160.

For example, when sensitivity, measurement time, time between measurements and the like are set to the blood pressure sensor 166, a plurality of parameters used to adjust these settings are contained in the sensor parameters, P of the blood sensor 166.

As illustrated in FIG. 7, in the table of parameters for modules, the information services which can be provided by the mobile station 2 and fixed terminal 4 and the service execution parameters P' which are used for its process in the service execution module 300 used for the implementation of each information service are associated with each other and stored.

The service execution parameters P' indicate, for example as stated above, the normal body temperature and pulse of the user of the mobile station 2 and fixed terminal 4 when a health check is provided as an information service.

In addition, for example as stated above, a constant number for the creation of position information by the integral treatment in the direction sensor 178 and accelerated velocity sensor 180 by the service execution module 300 and map information which is associated with the position information and displayed are contained in the service execution parameters P' when a navigation service is provided as an information service.

Furthermore, in the table of information creation parameters, as is the case with the table of parameters for modules shown in FIG. 7, the information services (Services) which can be provided by the mobile station 2 and fixed terminal 4 and the information creation parameters P' (Parameters for Modules) used for its process in the information creation module 310 used for the implementation of each information service are associated with each other and stored.

The information creation parameters P' indicate, for example, an image format for displaying an information service to the output device 148.

The module DB 254 stores the service execution module 300 and information creation module 310 (FIG. 5) used for the information services which can be provided by the mobile station 2 and fixed terminal 4 in such a way that they are accessible from the module selection unit 252 and information acquiring unit 262.

The module selection unit 252 selects and readouts the service execution module 300 and information creation module 310 used only for the information service that is determined to be implementable by the module execution control unit 266 within the specified information services on the basis of the information notified from the input analyzing unit 240, and loads into the module execution control unit 266.

The sensor drive module DB 274 stores the sensor drive module 286 adapted to the sensor 160 used for the information service which can be provided by the mobile station 2 and fixed terminal 4 in such a way that it is accessible from the sensor selection unit 272.

The sensor selection unit 272 selects and readouts the sensor drive module 286 used only for the information service that is determined to be implementable by the module execution control unit 266 within the specified information services on the basis of the information notified from the input analyzing unit 240 and outputs to the sensor control unit 270.

In addition, the sensor selection unit 272 determines if the combination of sensors 160 needed for obtaining the sensor data capable of improving the accuracy, speed of response, degree of detail, and the like of the specified information service is available, and notifies the combination of sensors 160 that is determined to be available to the parameter setting unit 246.

For example, in a health check service, if one blood pressure sensor 166, one pulse sensor 164 and two brain wave sensors 168 are available, in a case where the best result can be obtained and when not all of these are available, but only each of one blood pressure sensor 166 and pulse sensor 164 is available, the sensor selection unit 272 determines that the combination of these two sensors is available, and notifies to the parameter setting unit 246.

The sensor control unit 270 sets the sensor parameters, P set by the parameter setting unit 246 to the sensor drive module 286 input from the sensor selection unit 272 and executes so as to operate the sensor 160.

The sensor 160 is operated by the sensor drive module 286 and detects the information pursuant to each kind, and returns the detected result to the sensor drive module 286.

The sensor control unit 270 outputs the detected result input from the sensor 160 to the sensor output processing unit 278 as the information of sensor.

The sensor output processing unit 278 loads the information of sensor, which is input from the sensor drive module 286, into the module execution control unit 266.

In addition, the module execution control unit 266 processes the notification from the input analyzing unit 240, and when the other information service has been already executed, determines whether a duplication occurs in the resource needed for the implementation of these between a newly specified information service and an already executed information service, and estimates the throughput needed for each information service.

The module execution control unit 266 determines which information service would be implementable according to the duplication of the resource between the newly specified information service and the already implemented information service, the processing capacity needed for the implementation of each information service, and the remaining processing capacity of the mobile station 2 and fixed terminal 4, which is obtained from the OS operable on the mobile station 2 and fixed terminal 4, and notifies an information service that is determined to be implementable to the parameter setting unit 246, module selection unit 252 and sensor selection unit 272.

The module execution control unit 266 sets the service execution module 300 and information creation module 310 loaded from the sensor 160 (sensor drive module 286) and module selection unit 252 on the basis of the information indicating these input-output relations input from the input analyzing unit 240 so as to perform input and output for the implementation of an implementable information service within the specified services.

In addition, the module execution control unit 266 sets the service execution parameters P' and information creation parameters P' input from parameter setting unit 246 to the loaded the service execution module 300 and information creation module 310.

The module execution control unit 266 executes the service execution module 300 and information creation module 310 to which these settings have been performed, and implements one or more information services.

Furthermore, the module execution control unit 266 outputs the result of the information service of the implemented information service to the information creating unit 258.

The information creating unit 258 creates the information for outputting to a user from the result of the information service input from the module execution control unit 266, and outputs the information output unit 232 of the service providing unit 22.

[Server Program 60]

Hereinafter, a server program 60 executed in the module-parameter server device 6 shown in FIG. 1 will be described.

Figure 9:
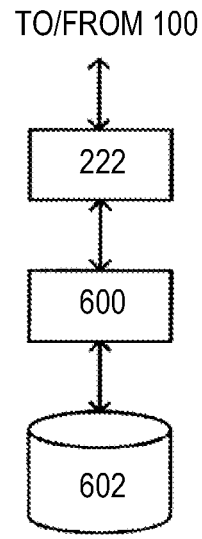
FIG. 9 is a diagram showing a server program executed in the server device shown in FIG. 1.

FIG. 9 is a diagram showing a server program 60 executed in the module-parameter server device 6 shown in FIG. 1.

As illustrated in FIG. 9, the server program 60 includes a communication processing unit 222, a DB searching unit 600 and a module-parameter DB 602.

The server program 60 receives a request from the mobile station 2 and fixed terminal 4 by these component parts, and returns the requested modules and parameters.

In the server program 60, the module-parameter DB 602 stores modules and parameters needed for the information services provided in the mobile station 2 and fixed terminal 4 in such a way that they can be referenced from the DB searching unit 600.

The DB searching unit 600 readouts one or more of the modules and parameters requested from the mobile station 2 and fixed terminal 4 from the module-parameter DB 602, and transmits to the mobile station 2 and fixed terminal 4 through the communication processing unit 222 and network 100.

[Web Program 80]

Hereinafter, a Web program 80 executed in the Web server 8 shown in FIG. 1 will be described.

Figure 10:
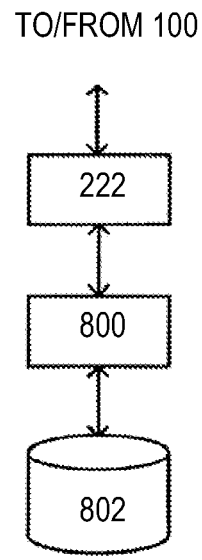
FIG. 10 is a diagram showing a Web program executed in the Web server shown in FIG. 1.

FIG. 10 is a diagram showing a Web program 80 executed in the Web server 8 shown in FIG. 1.

As illustrated in FIG. 10, the Web program 80 includes a communication processing unit 222, a Web data distribution unit 800 and Web content DB 802.

The Web program 80 receives a request from the mobile station 2 and fixed terminal 4 by these component parts, and returns requested Web content.

In the Web program 80, the Web content DB 802 stores the Web content provided to the mobile station 2 and fixed terminal 4 and displayed in such a way that the content is accessible by the Web data distribution unit 800.

The Web data distribution unit 800 readouts Web content from the Web data distribution unit 800 upon request from the mobile station 2 and fixed terminal 4, and transmits to the mobile station 2 and fixed terminal 4 which have requested through the service providing unit 22 and network 100.

[The Operation of an Information Service Providing System 1 in First Embodiment]

Hereinafter, the operation of an information service providing system 1 in the first embodiment will be described.

Figure 11A:
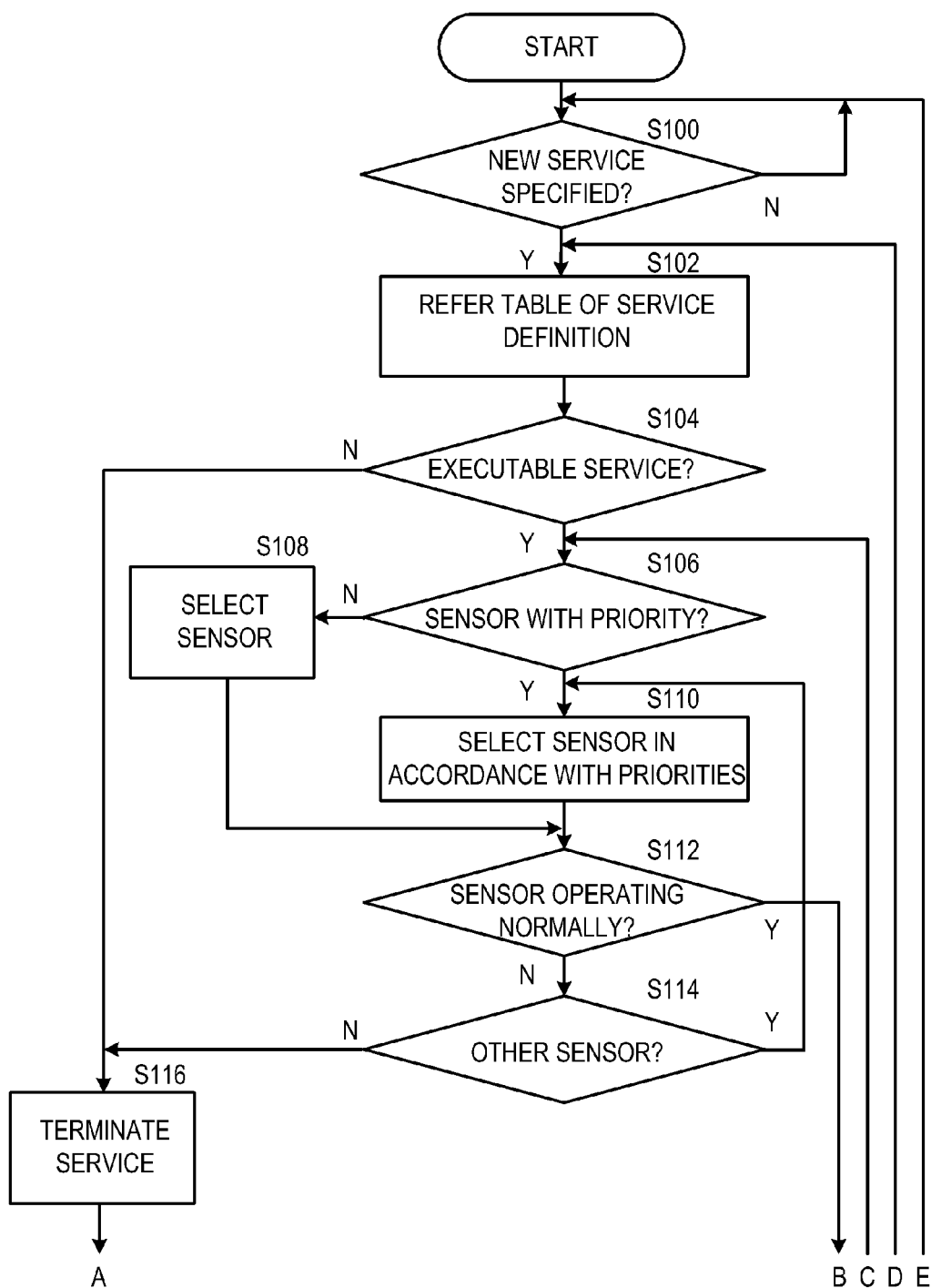
FIG. 11A is a first flow chart illustrating an operation in the first embodiment of the information service providing system shown in FIG. 1.
Figure 11B:
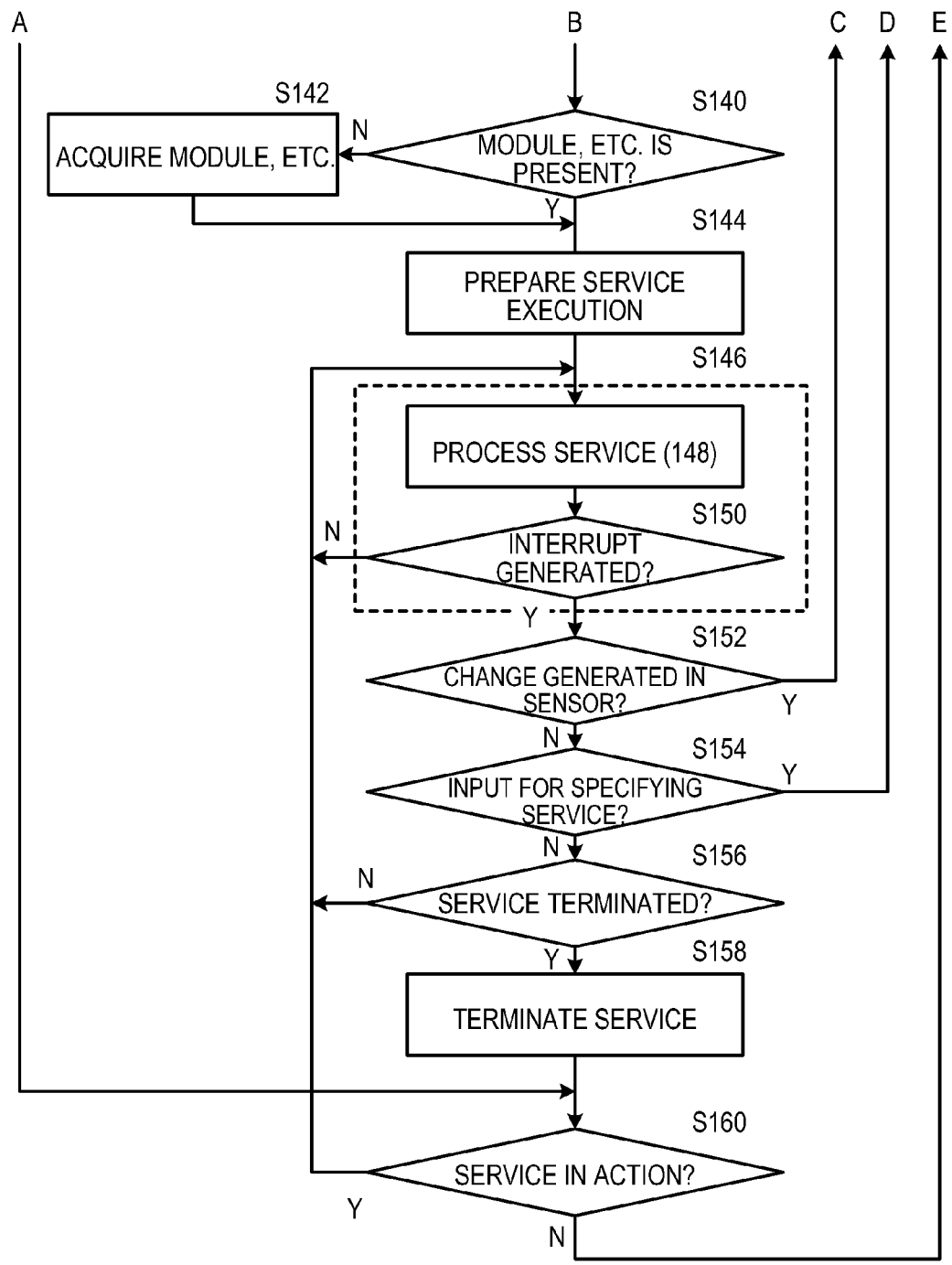
FIG. 11B is a second flow chart illustrating an operation in the first embodiment of the information service providing system shown in FIG. 1.

FIG. 11A, FIG. 11B are the first and second flow charts showing an operation S10 in the first embodiment of the information service providing system 1 shown in FIG. 1, respectively.

In addition, A-E shown in FIG. 11A, FIG. 11B represent that lines to which the same reference sign is assigned are connected and indicate the process flow among these figures.

As illustrated in FIG. 11A, FIG. 11B, in step 100 (S100), when a terminal program 20 (FIG. 4) is activated in the mobile station 2 and fixed terminal 4 and a server program 60 (FIG. 9) is activated in the module-parameter server device 6, the application input unit 230 of the terminal program 20 determines if an operation for specifying a new information service is performed to the input device 146 (UI 220) by the user of the mobile station 2 and fixed terminal 4.

The terminal program 20 proceeds to the process of S102 when the operation is performed, and, in other cases, stays in the process of S100.

In step 102 (S102), the input analyzing unit 240 receives the designation of an information service through the application input unit 230, references the table of service definition (FIG. 6) stored in the input analyzing DB 242, requests which modules and parameters would be needed for the implementation of the specified service, and notifies to the module execution control unit 266 or the like.

Furthermore, the module execution control unit 266 processes the notification from the input analyzing unit 240, and when the other information service has been already executed, determines whether a duplication occurs in the resource needed for the implementation of these between a newly specified information service and an already executed information service.

In addition, the module execution control unit 266 estimates the throughput needed for a newly specified information service.

In addition, the sensor selection unit 272 determines if the combination of sensors 160 needed for obtaining the sensor data capable of improving the accuracy, speed of response, degree of detail, and the like of the specified information service is available.

In step 104 (S104), the module execution control unit 266 determines whether each information service is executable on the basis of the abovementioned determined duplication of the resource, the remaining processing capacity of the mobile station 2 and fixed terminal 4, which can be obtained from the OS executed on the mobile station 2 and fixed terminal 4, the above-mentioned estimated throughput and the priority of each information service defined in the table of service definition.

The terminal program 20 proceeds to the process of S106 when there is an inexecutable information service and the module execution control unit 266 and sensor control unit 270 performs the process for termination the execution of the inexecutable information service (S106), and, in other cases, proceeds to the process of S106.

In step 106 (S106), the sensor selection unit 272 determines whether a priority is assigned to the sensor 160 needed for the implementation of a newly specified information service in the table of service definition (FIG. 6).

The terminal program 20 proceeds to the process of S110 when a priority is assigned to the sensor 160, and, in other cases, proceeds to the process of S108.

In step 108 (S108), the sensor selection unit 272 selects a sensor 160 (sensor drive module 286) needed for the implementation of a newly specified information service in the table of service definition (FIG. 6).

In addition, the sensor selection unit 272 determines whether the combination of sensors 160 needed for obtaining the sensor data capable of optimizing the accuracy, speed of response, degree of detail, and the like of the specified information service is available.

When not available, the combination of sensors having the next priority in the same information service is determined whether it is available.

In step 110 (S110), the sensor selection unit 272 selects a sensor 160 which has not been subjected to the process of S110 at the time, and to which the highest priority is assigned in the table of service definition within the available sensors 160 which are needed for the implementation of a newly specified information service and available.

In step 112 (S112), the sensor control unit 270 determines whether the selected sensor 160 normally operates in the process of S110.

When the sensor 160 normally operates (for example, when GPS 176 normally receives radio signals in a navigation service), the sensor control unit 270 proceeds to the process of S140, and, in other cases, proceeds to the process of S114.

In step 114 (S114), the sensor selection unit 272 determines whether the other sensor 160 which has not been subjected to the process of S110 at the time is present within the sensors 160 needed for the implementation of a newly specified information service.

The terminal program 20 returns to the process of S110 when the other sensor 160 is present, and, in other cases, proceeds to the process of S116, and the module execution control unit 266 and sensor control unit 270 performs the process for terminating the newly specified information service.

In step 140 (S140), the information acquiring unit 262 determines whether all of the modules and parameters (FIG. 5-FIG. 7) needed for the implementation of a newly specified information service is present in the terminal program 20.

The terminal program 20 proceeds to the process of S142 when all of the needed modules and parameters are present in the terminal program 20, and, in other cases, proceeds to the process of S144.

In step 142 (S142), the module execution control unit 266 sets the parameter input from the parameter DB 248 to the module loaded from the module selection unit 252, and prepares the execution of an information service by setting the information to be delivered among the module, middleware 24 and sensor driving unit 28 suitably for the implementation of a newly specified information service.

In step 146 (S146), the module execution control unit 266 performs the process for the implementation of each information service, and outputs the result of each information service as appropriate through the information creating unit 258 and UI 220 (S148).

While performing the process for the implementation of each information service, the module execution control unit 266 determines whether the interrupt signal and notification from an OS, which indicate such as the designation of a new information service, that a sensor 160 (sensor drive module 286) which has normally operated does not operate, or that a sensor 160 which has not normally operated starts to operate normally, is generated (S150).

The module execution control unit 266 proceeds to the process of S152 when an interrupt is generated, and, in other cases, stays in the process of S146.

In step 152 (S152), the module execution control unit 266 determines whether a change is generated in the state of a sensor 160 (sensor drive module 286) operating for the implementation of each information service.

Thus, the module execution control unit 266 determines whether an event associated with the change of the state of a sensor, in which, a sensor 160 (sensor drive module 286) which has normally operated does not normally operate, or, a sensor 160 which has not normally operated starts to operate normally, is generated for the implementation of each information service.

When an event associated with the change of the state of a sensor used for the implementation of an information service is generated, the terminal program 20 sets the sensor 160 used in the implementation of this information service to the state which has not been subjected to the process of S110 and returns to the process of S106, and, in other cases, proceeds to the process of S154.

In step 154 (S154), the module execution control unit 266 determines whether the generation of an interrupt or the like detected in S148 is the designation of a new service.

The terminal program 20 proceeds to the process of S102 when the generation of an interrupt or the like indicates the designation of a new service, and, in other cases, proceeds to the process of S156.

In step 156 (S156), the module execution control unit 266 determines whether the generation of an interrupt or the like detected in S148 indicates the termination of an information service in action.

The terminal program 20 proceeds to the process of S158 when the generation of an interrupt or the like indicates the termination of an information service in action, and, in other cases, performs a process associated with the generation of an interrupt or the like as appropriate, and returns to the process of S146.

In step 158 (S158), the module execution control unit 266 performs the process for terminating an information service which is determined that it should be terminated in the process of S156.

In step 160 (S160), the module execution control unit 266 determines whether there is an information service in action other than the information service terminated in the process of S158.

The terminal program 20 returns to the process of S146 when an information service in action exists, and, in other cases, returns to the process of S100.

[Example of Information Service]

Hereinafter, the first and second information services provided by the mobile station 2 and fixed terminal 4 will be illustrated.

In addition, in FIG. 6-FIG. 7, the table of service definition, table of sensor parameters, table of parameters for modules and table of information creation parameters for implementing the following three examples are illustrated.

In addition, each information service shown below is an illustrative example, and an information service which may be provided by the mobile station 2 and fixed terminal 4 is not limited to these three kinds.

[Health Check]

Hereinafter, giving the provision of a first health check for checking user's health condition by the mobile station 2 and fixed terminal 4 as an illustrative embodiment, the operation of the mobile station 2 and fixed terminal 4 will be described.

Figure 12:
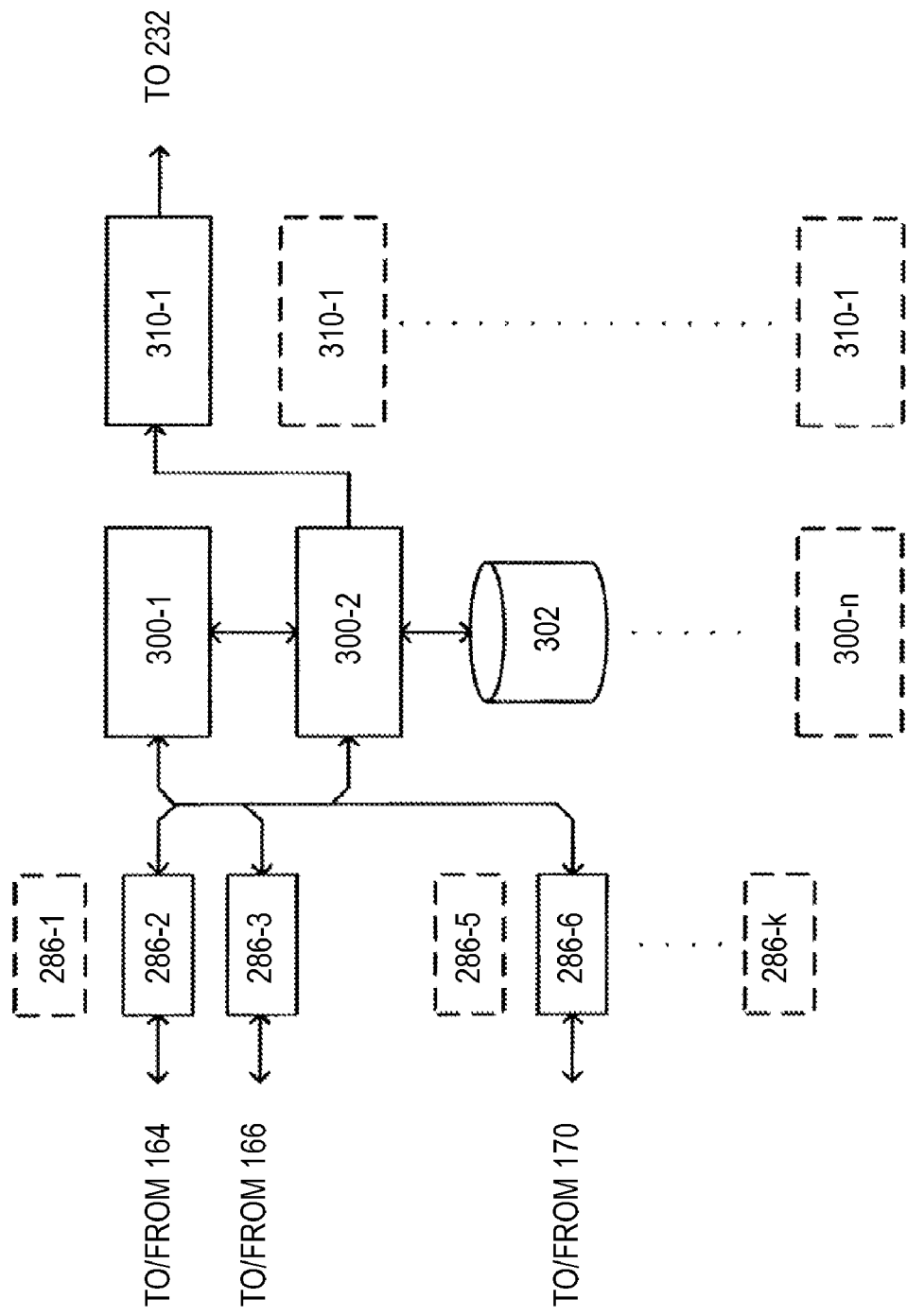
FIG. 12 is a diagram illustrating a first information service (health check) provided by the mobile station and fixed terminal shown in FIG. 1.

FIG. 12 is a diagram illustrating a first information service (health check) provided by the mobile station 2 and fixed terminal 4.

As illustrated in FIG. 12, when the mobile station 2 and fixed terminal 4 implement a health check as an information service, for example, the pulse sensor 162, blood pressure sensor 166 and body temperature sensor 172 are selected as the sensor 160, and sensor drive modules 286-1, 286-2 and 286-5 adapted to these are loaded to the sensor control unit 270 and executed.

In addition, for example, the information of sensor, which indicate the physical information such as the pulse rate, blood pressure and body temperature of a user is periodically collected from the sensor 160 as the information of sensor, and a service execution module 300-1 which creates the numeric values for comprehensively indicating these information is loaded to the module execution control unit 266.

Furthermore, the numeric values created by the service execution module 300-1 is compared with determination data 302 set as the service execution parameters, and a service execution module 300-2 which comprehensively determines the health of the user of the mobile station 2 and fixed terminal 4 is loaded to the module execution control unit 266.

Furthermore, an information creation module 310-1 which creates the result of the health check of a predetermined image format from the determination result of the service execution module 300-2 is loaded to the module execution control unit 266.

The module execution control unit 266 inputs the information of sensor from the sensor drive modules 286-1, 286-2, and 286-5 to the service execution module 300-1 so as to cause the service execution module 300-1 to process the information, and outputs the processing result to the information creation module 310-2.

The service execution module 300-2 determines the processing result input from the service execution module 300-1, and outputs the determination result to the information creation module 310.

The information creation module 310-1 creates the result of the health check in a predetermined format from the determination result input from the service execution module 300-1, outputs to the information output unit 232 (FIG. 4) through the information creating unit 258, and displays to the user.

In addition, the information creation module 310-1 may display the physical information obtained from the sensor 160 to the output device 148 along with the determination result.

Furthermore, a plurality of kinds of health checks can be provided.

For example, for a health check emphasizing on user's cardiac motion, the table of service definition (FIG. 6) is set in order for the pulse sensor 162, blood pressure sensor 166, perspiration sensor 162, cardiac signal sensor 170, body temperature sensor 172, blood component sensor 174 and temperature-humidity sensor 184 to be used as the sensor 160, and parameters appropriate for this purpose may be set to the table of sensor parameters, table of parameters for modules and table of information creation parameters.

In this case, for example, the highest priority 1 to the cardiac signal sensor 170, the next priority 2 to the pulse sensor 162 and blood pressure sensor 166, and the lowest priority 3 to the other sensor 160 are set in the table of parameters for modules as a priority for each sensor 160 to be used.

In addition, for example, similarly, for a health check emphasizing on the amount of exercise of user, the pulse sensor 162, perspiration sensor 164, cardiac signal sensor 170, body temperature sensor 172, pedometer 188, body temperature sensor 172, accelerated velocity sensor 180 and speed sensor 182 are set to the table of parameters for modules so as to be used.

In this case, for example, within the sensors 160 to be used, the highest priority 1 is set to the pulse sensor 162, pedometer 188, cardiac signal sensor 170 and body temperature sensor 172, and the next priority 2 is set to other sensor 160.

In addition, for example, for a health check emphasizing on the state of the brain of user, the blood pressure sensor 166, brain wave sensor 168, cardiac signal sensor 170, body temperature sensor 172 and blood component sensor 174 are set to the table of parameters for modules so as to be used.

In this case, for example, within the sensors 160 to be used, the highest priority 1 to the brain wave sensor 168, the next priority 2 to the cardiac signal sensor 170 and blood component sensor 174, and the lowest priority 3 to the other sensor 160 are set.

In addition, for example, in a health check service, there are cases wherein when one blood pressure sensor 166, one pulse sensor 164 and two brain wave sensors 169 (first combination) are used, the best result is obtained, when one blood pressure sensor 166 and pulse sensor 164 (second combination) are used, the second-best result is obtained, and when only one blood pressure sensor 166 (third combination) is used, the third-best result is obtained.

In such a case, priorities are set to the combination of sensors 160 in such a way that the highest priority 1 is set to the first combination, the next priority 2 is set to second combination and the lowest priority 3 is set to the third combination.

[Navigation Service]

Hereinafter, giving a navigation service for displaying the location of the mobile station 2 and fixed terminal 4 on a map as an illustrative embodiment, the operation of the mobile station 2 and fixed terminal 4 will be described.

Figure 13:
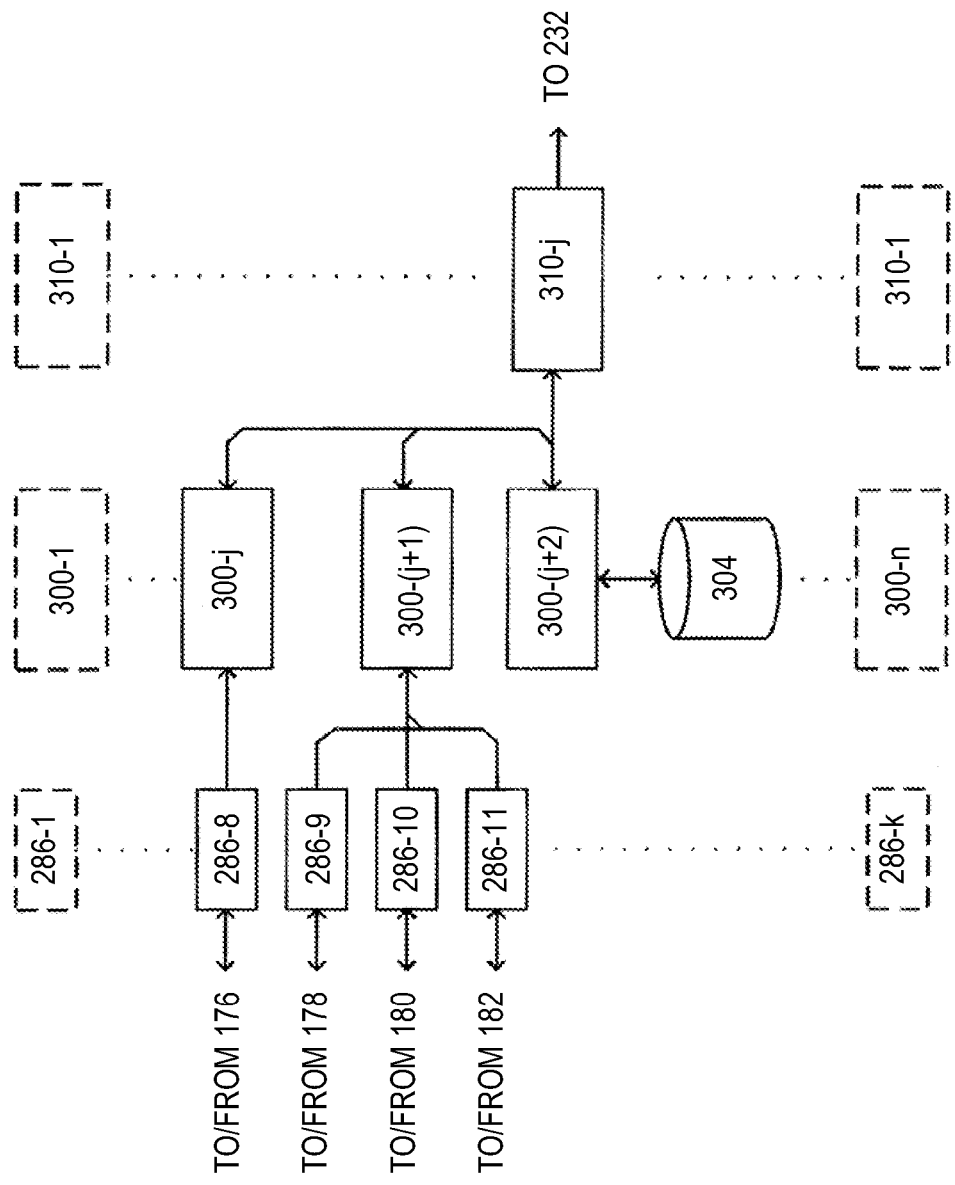
FIG. 13 is a diagram illustrating a second information service (navigation service) provided by the mobile station and fixed terminal shown in FIG. 1.

FIG. 13 is a diagram illustrating a second information service (navigation service) provided by the mobile station 2 and fixed terminal 4.

As illustrated in FIG. 13, in a case where the mobile station 2 and fixed terminal 4 provide a navigation service as an information service, for example, the GPS 176, direction sensor 178, accelerated velocity sensor 180 and speed sensor 182 are selected as a sensor 160, and sensor drive modules 286-8, 286-9, 286-10, and 286-11 adapted to these are loaded to the sensor control unit 270 and executed.

In addition, for example, a service execution module 300-$j$ which obtains the latitude/longitude of the mobile station 2 and fixed terminal 4 from the information of sensor input from the GPS 176 is loaded to the module execution control unit 266.

In addition, a service execution module 300-($j$+1), which processes the information of sensor input from the direction sensor 178, accelerated velocity sensor 180 and speed sensor 182 with integral treatment so as to obtain the latitude/longitude of the mobile station 2 and fixed terminal 4, is loaded to the module execution control unit 266.

In addition, a service execution module 300-($j$+2), which creates map data corresponding to the latitude/longitude from the service execution module 300-$j$ when map data 304 is set as the service execution parameters and the GPS 176 normally operates and creates map data corresponding to the latitude/longitude from the service execution module 300-($j$+1) when the GPS 176 does not normally operate, is loaded to the module execution control unit 266.

Furthermore, an information creation module 310-$j$, which creates the result of the navigation service in a predetermined format from the map data create by the service execution module 300-($j$+2), is loaded to the module execution control unit 266.

When a GPS 176 with a priority higher than that of the direction sensor 178, accelerated velocity sensor 180 and speed sensor 182 normally operates, the 6 module execution control unit 266 causes the service execution module 300-*j* to process the information of sensor from the sensor drive module 286-8, and outputs the processing result to the information creation module 310-*j*.

When the GPS 176 does not normally operate, the module execution control unit 266 causes the service execution module 300-(*j*+1) to process the information of sensor from the sensor drive modules 286-9, 286-10 and 286-11 corresponding to the direction sensor 178, accelerated velocity sensor 180 and speed sensor 182, and outputs the processing result to the service execution module 300-(*j*+2).

When the GPS 176 returns from the state of not normally operating to the state of normally operating, the module execution control unit 266 causes the service execution module 300-*j* to process the information of sensor from the sensor drive module 286-8 again, and outputs the processing result to the service execution module 300-(*j*+2).

The service execution module 300-(*j*+2) creates map data corresponding to the processing result (latitude/longitude) input from the service execution module 300-*j* or service execution module 300-(*j*+1), and outputs to the information creation module 310-*j* as a processing result.

The information creation module 310-*j* creates the result of the navigation service in a predetermined format from the map data input from the service execution module 300-(*j*+2), and outputs to the information output unit 232 (FIG. 4) through the information creating unit 258 and displays to the user.

In addition, it is possible that a navigation service using the GPS 176 and a navigation service using the direction sensor 178, accelerated velocity sensor 180 and speed sensor 182 are defined in the table of service definition or the like as a different information service, thereby implementing any service by a designation of user.

[Image Information Creating Service]

Hereinafter, as an information service, giving the provision of an image information creating service which stores image data taken by a camera 150 (FIG. 2) or the like attaching the location where the image was taken, comments and the like as an illustrative embodiment, the operation of the mobile station 2 and fixed terminal 4 will be described.

Figure 14:
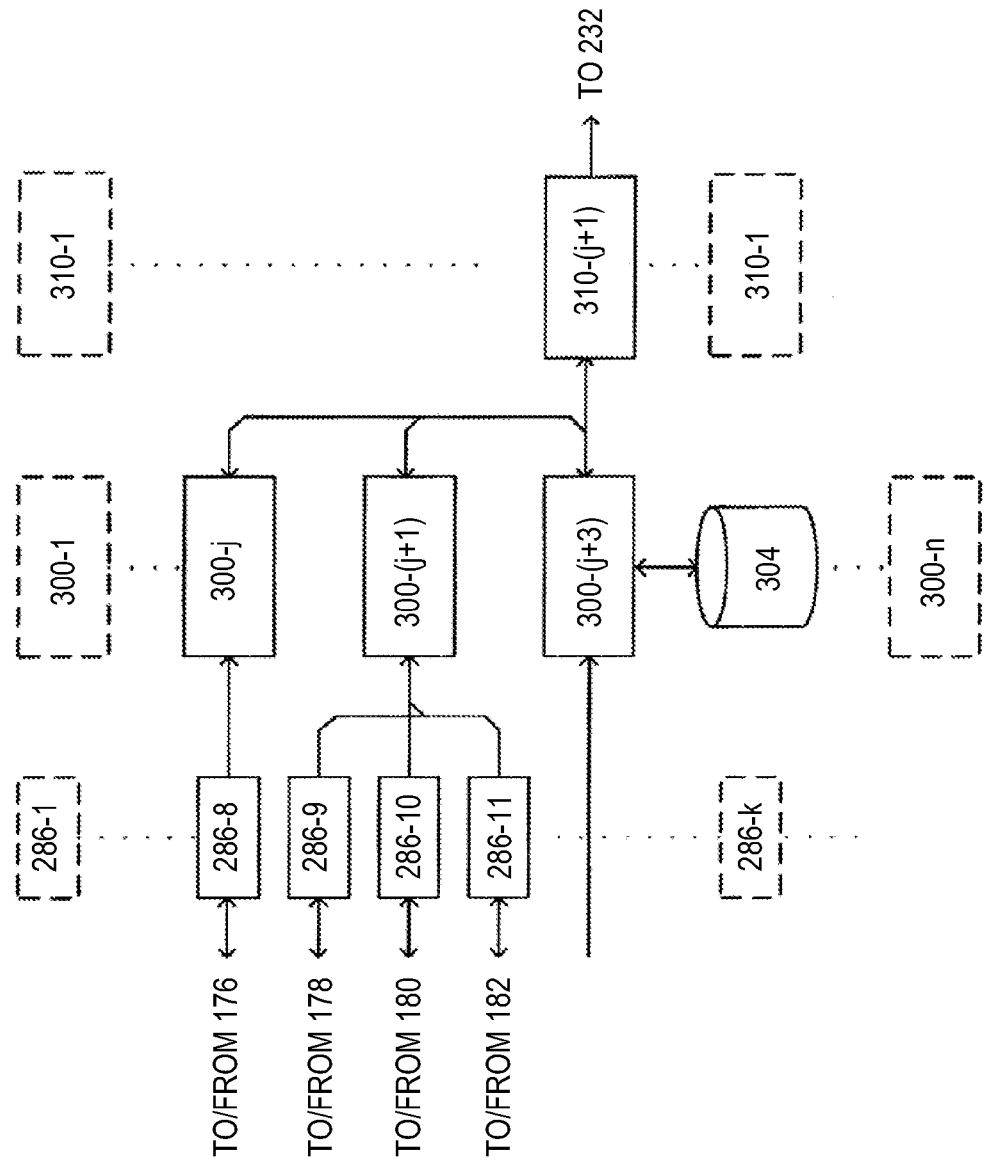
FIG. 14 is a diagram illustrating a third information service (image information creating service (Image Information)) provided by the mobile station and fixed terminal shown in FIG. 1.

FIG. 14 is a diagram illustrating a third information service (image information creating service (Image Data)) provided by the mobile station 2 and fixed terminal 4 shown in FIG. 1.

To provide the image information creating service, as alternatives to the service execution module 300-(*i*+2) and information creation module 310-*i* which are used in the navigation service, a service execution module 300-(*i*+3) and an information creation module 310-(*i*+1) are used.

In addition to the function of the service execution module 300-(*i*+2), the service execution module 300-(*i*+3) attaches, additional information such as the position information (latitude/longitude) of the mobile station 2 and fixed terminal 4, which is obtained by either of the service execution module 300-*i*, 300-(*i*+1), the map information indicating the location where the image was taken, and the comment statement input from the input device 146, to the dynamic image and static image taken by the camera 150, and outputs to the information creation module 310-(*i*+1) as the processing result.

In addition, this additional information may be attached to the images in any way and at any timing specified by the user through the input device 146.

For example, the additional information is attached to: each static image; a series (one scene) of each dynamic image; an image visibly; or an image invisibly.

The information creation module 310-(*i*+1) creates the result of a predetermined information service from the processing result input from the service execution module 300-(*i*+3), and outputs to the output device 148 through the information output unit 232, or stores in a memory 142, a memory card (not shown), or the like inserted into a CPU peripheral device 144.

In addition, in the table of service definition shown in FIG. 6, the sensors used in each of a plurality of kinds of health checks, a plurality of kinds of navigation services and a plurality of kinds of image information creating services, service execution module 300 and information creation module 310 may be defined. Furthermore, with regard to each of these services, appropriate parameters may be set to the table of sensor parameters, table of parameters for modules and table of information creation parameters, which are shown in FIG. 7 and FIG. 8.

In addition, the mobile station 2 used in the third information service shown here can be implemented with, for example, a digital camera alone, which is provided with sensors such as a GPS function and a pulse sensor 162 when the acquisition of modules and parameters from the module-parameter server device 6 is unnecessary.

By preparing settings of the definitions and parameters of the abovementioned plurality of kinds of health checks, various kinds of navigation services and various kinds of image information creating services and the sensor drive module 286, service execution module 300 and information creation module 310, which are appropriate for these information services, various kinds of health checks, the provision of various kinds of navigation services and various kinds of image information creating services is possible according to the designation of the user of the mobile station 2 and fixed terminal 4.

Similarly, besides the three kinds of information services described above, by preparing the settings of the definitions and parameters of information service and the sensor drive module 286, service execution module 300 and information creation module 310, which are needed for the provision of an information service, as appropriate, the provision of various kinds of information services other than these is possible.

[Second Embodiment]

Hereinafter, in the information service providing system 1, giving, as an information service, a Web browsing service designed to detect a component part of Web content, in which a user browsing Web content is interested by changing the operation of the terminal program 20 (FIG. 4) as an illustrative embodiment, the second embodiment of the disclosure of the present application will be described.

FIG. 15 is a second diagram illustrating a table of service definition, which is stored in the input analyzing DB 242 shown in FIG. 4.

The input analyzing DB 242 stores the second table of service definition shown in FIG. 15 in such a way that the input analyzing unit 240 can reference thereto.

Hereinafter, the difference between the first table of service definition shown in FIG. 6 and the second table of service definition shown in FIG. 15 will be further described.

In the second table of service definition, the information services which can be provided by the mobile station 2 and fixed terminal 4 (FIG. 1) and one or more of the combination of sensors 160 used in each of the providable information services (Services; S1-S#n) are associated with each other.

In addition, the priorities of the combination of sensors 160 to be used are indicated by the numbers such as 1, 2, 3 . . . , and a case where, a high priority 1 is set to the first combination (pulse sensor 162, perspiration sensor 164, brain wave sensor 168 and viewpoint detection sensor 186) of the sensor 160, and a low priority 2 is set to the second combination (pulse sensor 162 and perspiration sensor 164) of the sensor 160, both of which are used for the implementation of the abovementioned web browser (Web Browser) function S#m as an information service, is illustrated in FIG. 15.

FIG. 16 is a second diagram illustrating the table of sensor parameters, which is stored in the parameter DB 248 shown in FIG. 4.

FIG. 17 is a second diagram illustrating the table of parameters for modules, which is stored in the parameter DB 248 shown in FIG. 4.

The parameter DB 248 stores the table of sensor parameters shown in FIG. 16, the table of parameters for modules shown in FIG. 17 and the table of information creation parameters, the composition of which is similar to the table of parameters for modules shown in FIG. 17 in such a way that the stored table can be referenced from the parameter setting unit 246 and information acquiring unit 262.

In addition, as illustrated in FIG. 16, the sensor parameters, $P_{mp}$-$P_{m(p+1)}$ to be set to the sensor drive modules 286-1, 286-2, 286-4, 286-13 and service execution modules 300-$p$ to 300-($p$+2), which correspond to the pulse sensor 162, perspiration sensor 164, brain wave sensor 168 and viewpoint detection sensor 186, are set in the table of sensor parameters used for the implementation of the abovementioned web browser function.

In addition, as illustrated in FIG. 17, the service execution parameters and information creation parameters are set to each of the table of parameters for modules and table of information creation parameters, corresponding to the service execution module 300 and information creation module 310, which are used for the implementation of the abovementioned web browser function.

[The Operation of an Information Service Providing System 1 in Second Embodiment]

Hereinafter, the operation of an information service providing system 1 in the second embodiment will be described.

Figure 18A:
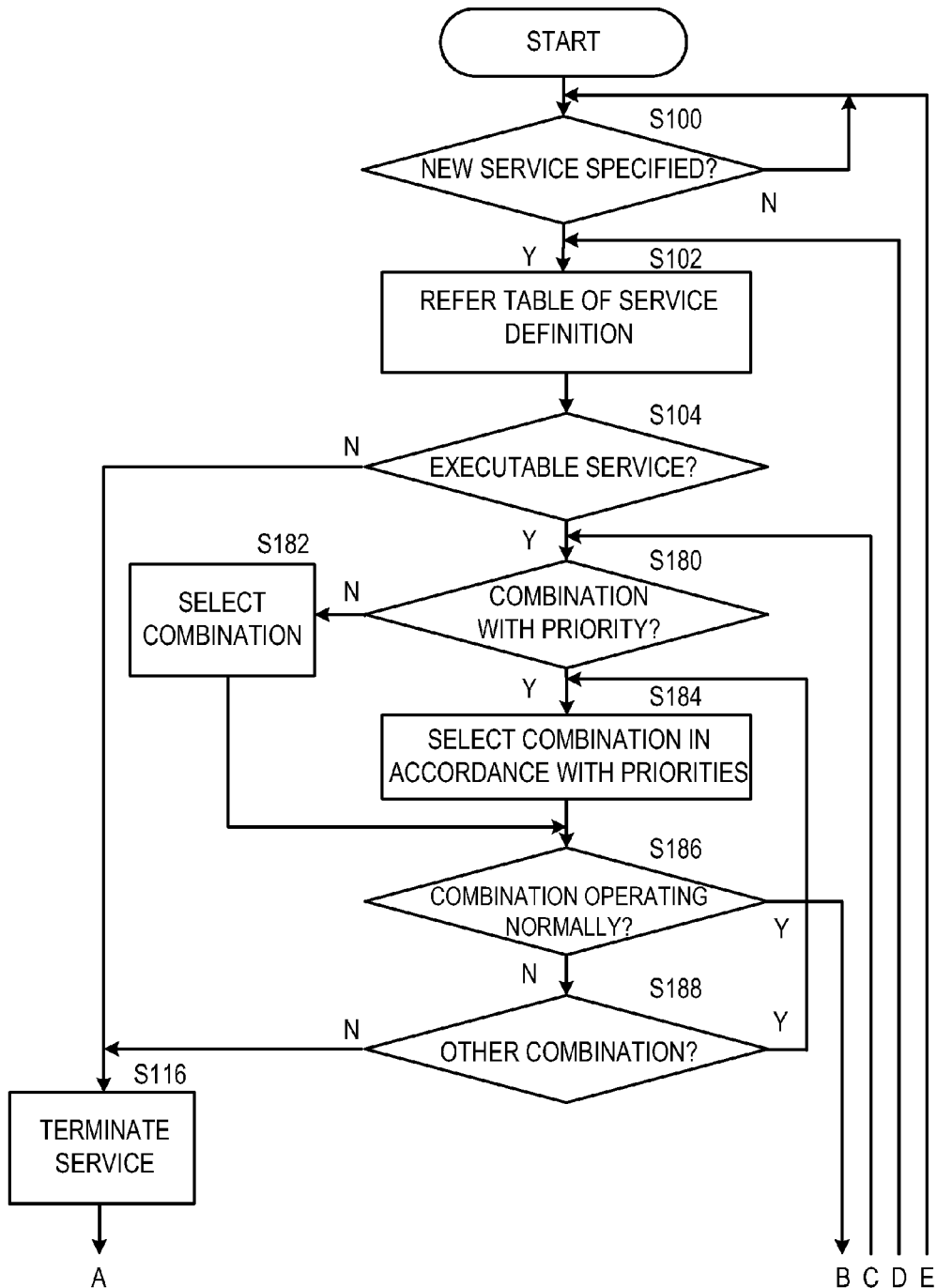
FIG. 18A is a first flow chart illustrating an operation (S18) in the second embodiment of the information service providing system shown in FIG. 1.
Figure 18B:
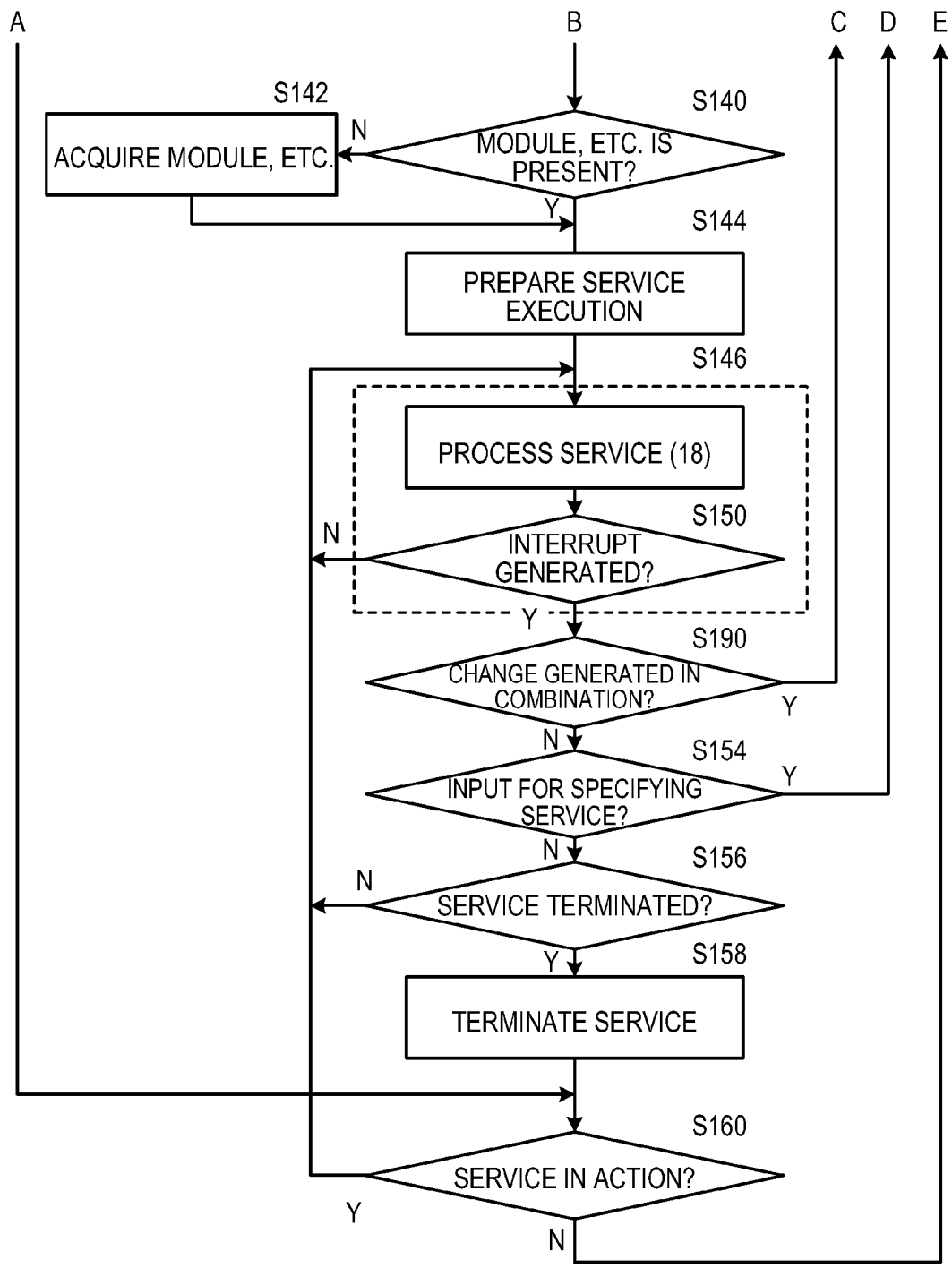
FIG. 18B is a second flow chart illustrating an operation (S18) in the second embodiment of the information service providing system shown in FIG. 1.

FIG. 18A, FIG. 18B are the first and second flow charts showing an operation (S18) in the second embodiment of the information service providing system 1 shown in FIG. 1.

[The Operation of an Information Service Providing System 1 in First Embodiment]

Hereinafter, the operation of an information service providing system 1 in the first embodiment will be described.

FIG. 11A, FIG. 11B are the first and second flow charts illustrating an operation S10 in the first embodiment of the information service providing system 1 shown in FIG. 1, respectively.

In addition, A-E shown in FIG. 11A, FIG. 11B represent that lines to which the same reference sign is assigned are connected and indicate the process flow among these figures.

As illustrated in FIG. 11A, FIG. 11B, when a terminal program 20 (FIG. 4) is activated in the mobile station 2 and fixed terminal 4, a server program 60 (FIG. 9) is activated in the module-parameter server device 6 and a Web program 80 (FIG. 10) is activated in a Web server 8, the terminal program 20 performs the process of S100 shown in FIG. 11A.

In step 102 (S102), the terminal program 20 performs a process similar to the process of S102 shown in FIG. 11A.

Thus, the input analyzing unit 240 of the terminal program 20 performs a process with reference to the table of service definition (FIG. 16), and the module execution control unit 266 performs a process for estimating the duplication and the throughput of the resource.

In step 104 (S104), the terminal program 20 performs a process similar to the process of S104 shown in FIG. 11A, and when an inexecutable information service is present, performs the process for terminating this (S106), and, in other cases, proceeds to the process of S180.

In step 180 (S190), the sensor selection unit 272 determines whether a priority is assigned to the combination of sensors 160 needed for the implementation of a newly specified information service in the table of service definition (FIG. 16).

The terminal program 20 proceeds to the process of S184 when a priority is assigned to the combination of sensors 160, and, in other cases, proceeds to the process of S182.

In step 182 (S182), the sensor selection unit 272 selects the combination of sensors 160 (sensor drive module 286) needed for the implementation of a newly specified information service in the table of service definition (FIG. 15).

In step 184 (S110), the sensor selection unit 272 selects the combination of sensors 160 which has not been subjected to the process of S180 at the time, and to which the highest priority is assigned in the table of service definition within the combination of sensors 160, which is needed for the implementation of a newly specified information service and available.

The sensor control unit 270 sets the sensor parameters, P (FIG. 16) input from the parameter DB 248 to the sensor 160 (sensor drive module 286) selected by the sensor selection unit 272 and activates the sensor.

In step S186 (S186), the sensor control unit 270 determines whether the all sensors contained in the combination of the sensors 160 (sensor drive module 286) activated in the process of S184 normally operate.

When the sensor 160 normally operates (for example, when all of the pulse sensor 162, perspiration sensor 164, brain wave sensor 168 and viewpoint detection sensor 186 normally operates), the sensor control unit 270 proceeds to the process of S140, and, in other cases, proceed to the process of S188.

In step 188 (S188), the sensor selection unit 272 determines whether the other combination of sensors 160 which has not been subjected to the process of S180 at the time is present within the combination of sensors 160 (sensor drive module 286) needed for the implementation of a newly specified information service.

The terminal program 20 returns to the process of S180 when the other combination of sensors 160 is present, and, in other cases, proceeds to the process of S116, and the module execution control unit 266 and sensor control unit 270 performs the process for terminating the newly specified information service.

In step 140 (S140), the terminal program 20 performs a process similar to the process of S140 shown in FIG. 11B.

In step 142 (S142), the terminal program 20 performs a process similar to the process of S142 shown in FIG. 11B.

In step 146 (S146), the terminal program 20 performs a process similar to the process of S146 shown in FIG. 11B.

Thus, the module execution control unit 266 performs the process for the implementation of each information service, and outputs the result of each information service (S148).

While performing the process for the implementation of each information service, the terminal program 20 determines whether an event such as that the state of a sensor has changed is generated (S150).

The module execution control unit 266 proceeds to the process of S190 when an interrupt is generated, and, in other cases, stays in the process of S146.

In step 190 (S190), the module execution control unit 266 determines whether a change is generated in the state of one or more of sensors 160 (sensor drive module 286) contained in the combination of sensors 160 (sensor drive module 286) operating for the implementation of each information service.

Thus, the module execution control unit 266 determines whether an event associated with the change of the state of a sensor, in which one or more the sensors 160 contained in the combination of sensors 160, which have normally operated do not normally operate, or, all of the sensors 160 contained in the combination of sensors 160, which has not normally operated starts to operate normally, is generated, for the implementation of each information service.

When an event associated with the change of the state of a sensor used for the implementation of an information service is generated, the terminal program 20 sets the combination of sensors 160 used in the implementation of this information service to the state which has not been subjected to the process of S180 and returns to the process of S180, and, in other cases, proceeds to the process of S154.

In step 154 (S154), the terminal program 20 performs a process similar to the process of S154 shown in FIG. 11B.

In step 156 (S156), the terminal program 20 performs a process similar to the process of S156 shown in FIG. 11B.

In step 158 (S158), the terminal program 20 performs a process similar to the process of S158 shown in FIG. 11B.

In step 160 (S160), the terminal program 20 performs a process similar to the process of S160 shown in FIG. 11B.

[Display of Web Content and Detection of Interest]

Hereinafter, a fourth information service provided by the mobile station 2 and fixed terminal 4 will be illustrated.

Figure 19:
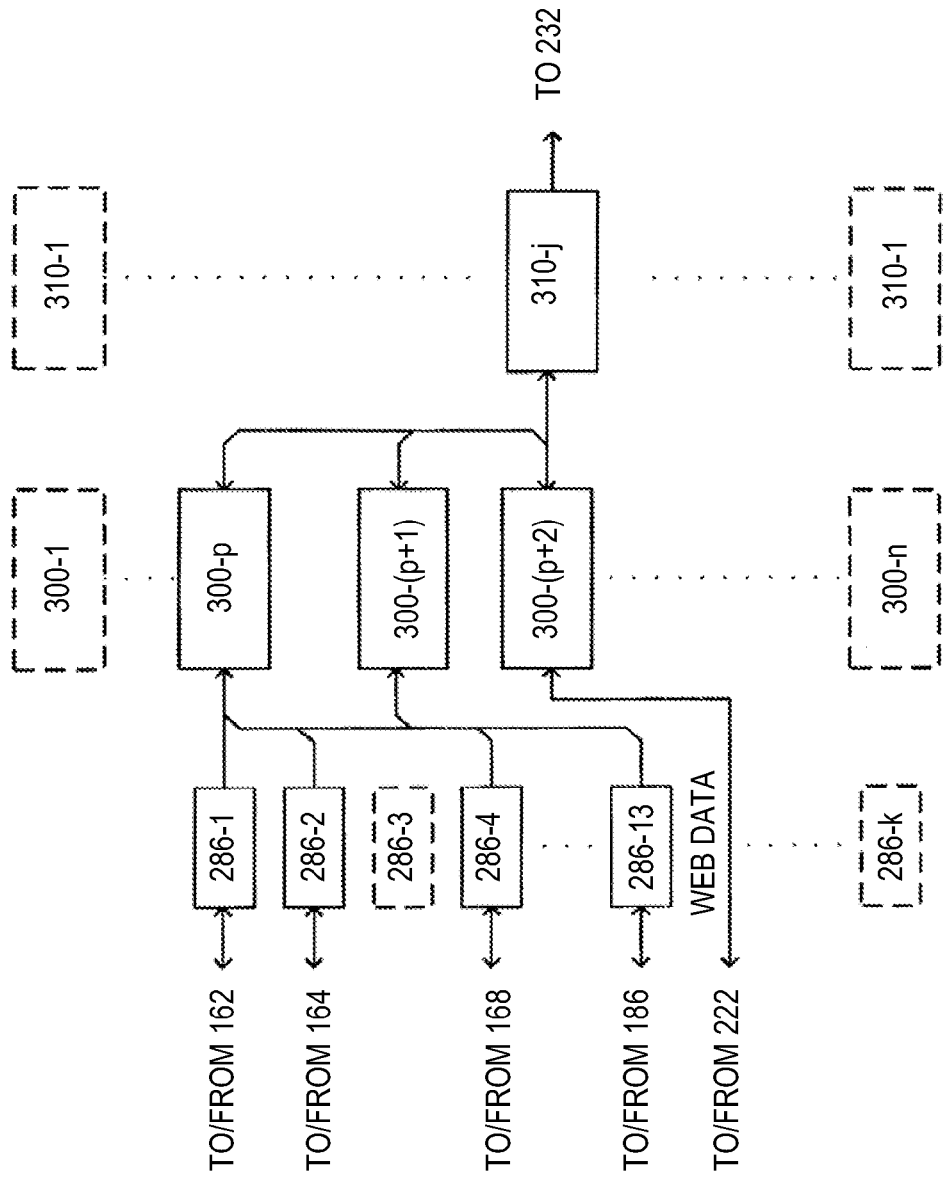
FIG. 19 is a diagram illustrating an information service for detecting the display of Web content and the presence or absence of user's interest in the component part of the Web content in the information service providing system.
Figure 4:
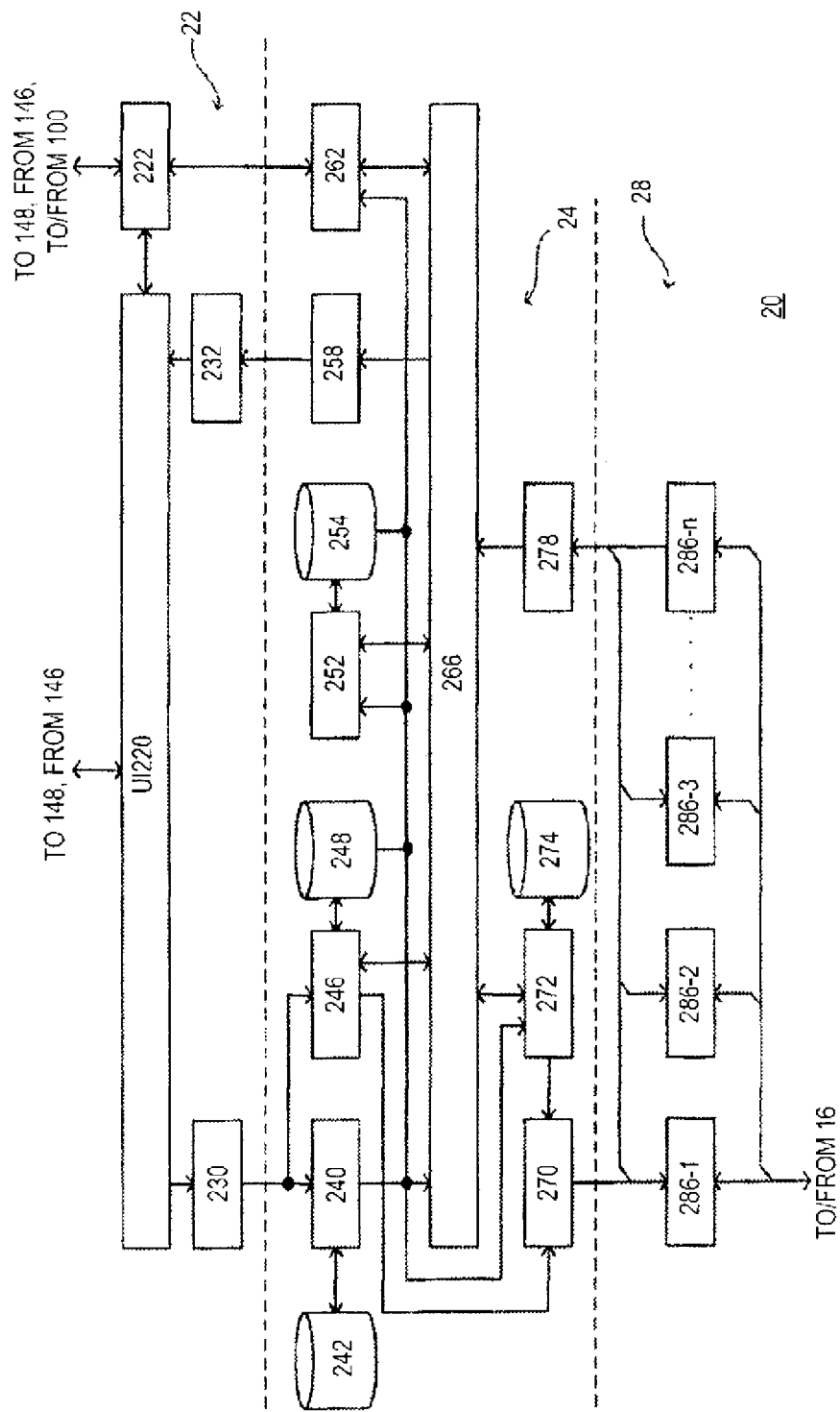
Figure 11A:
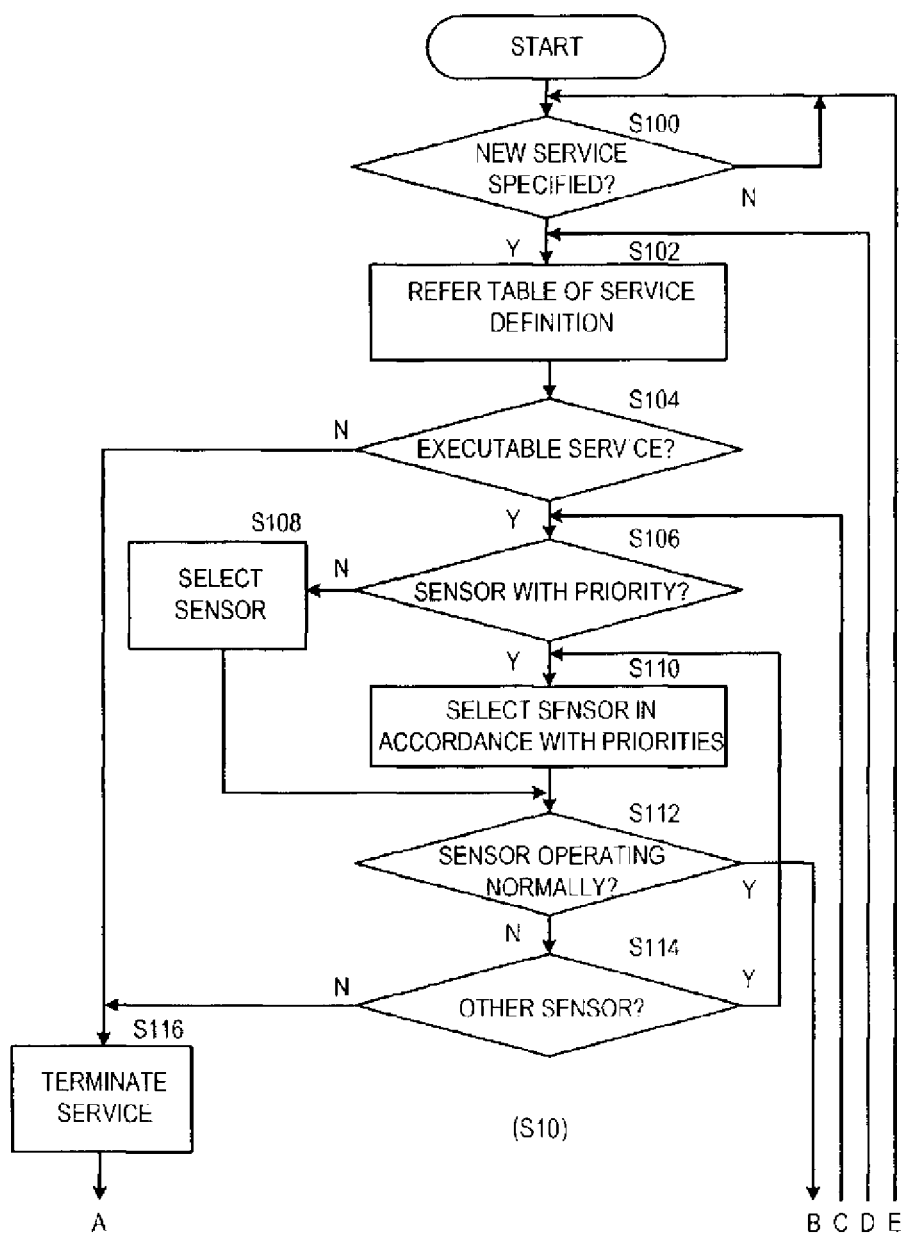
Figure 11B:
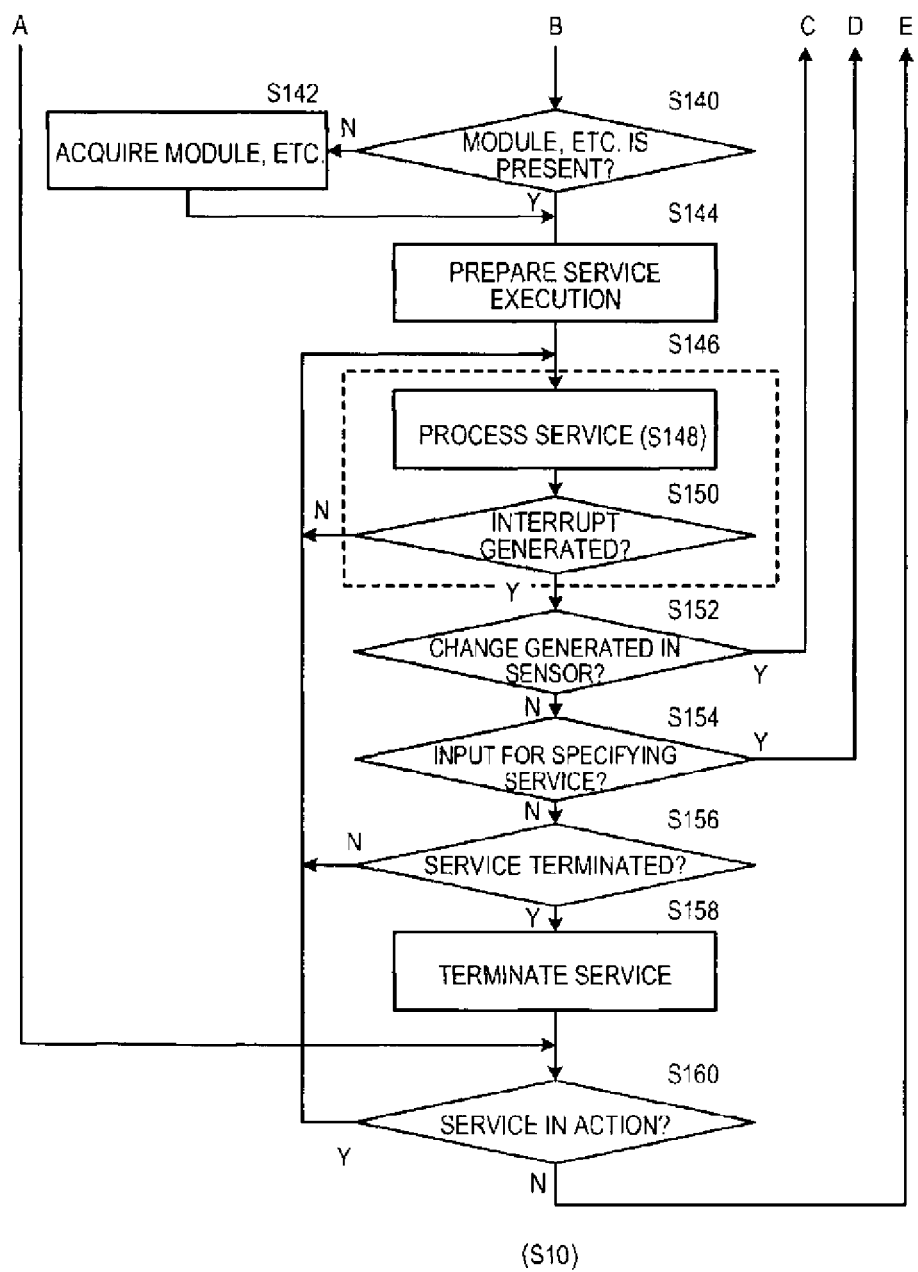
Figure 18A:
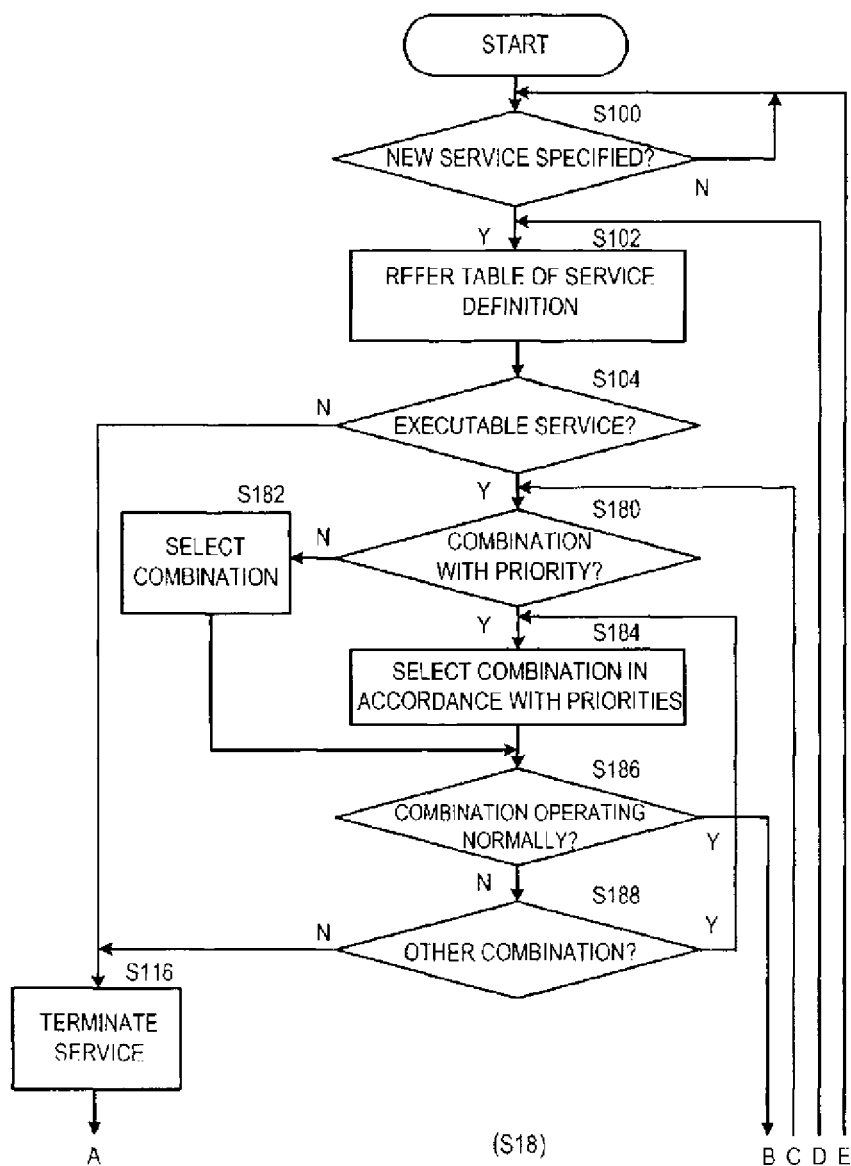
Figure 18B:
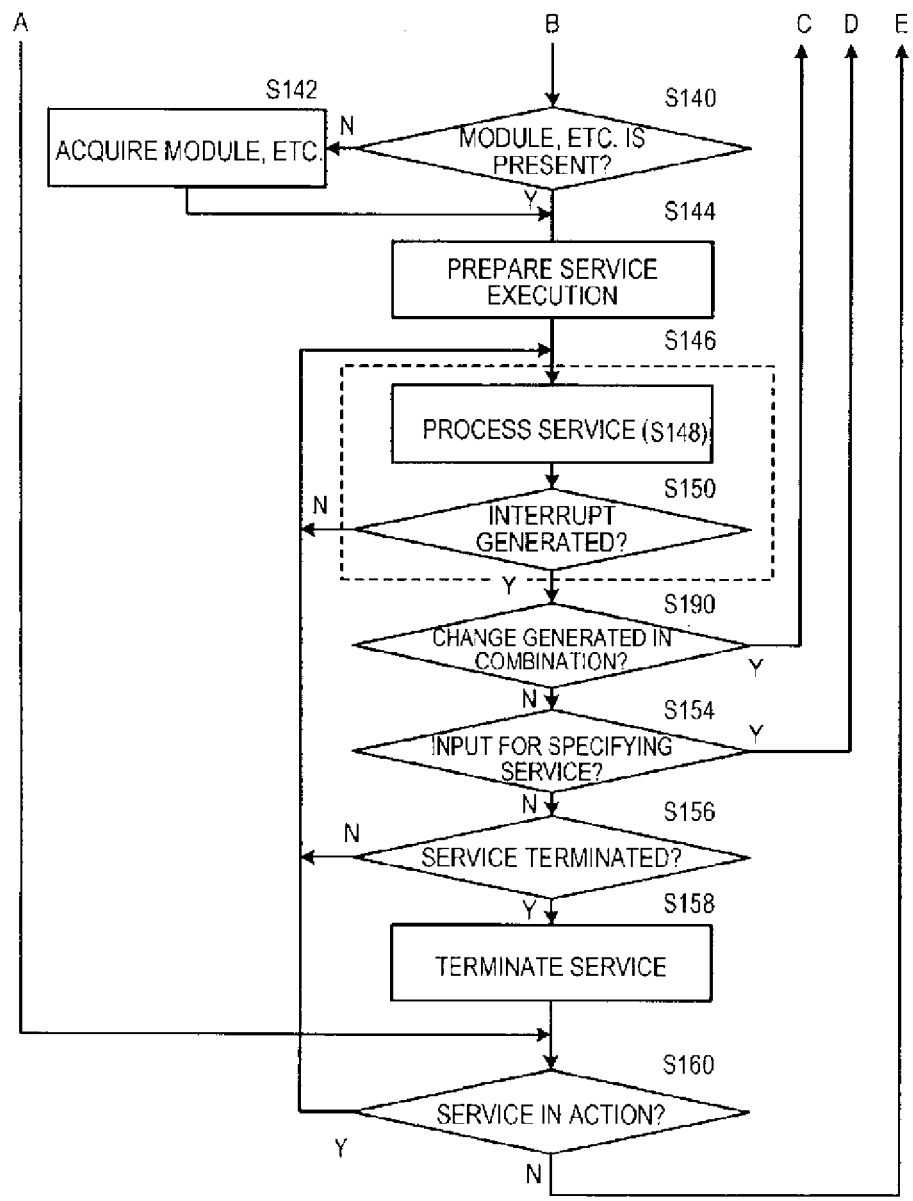

FIG. 19 is a diagram illustrating an information service for detecting the display of Web content and the presence or absence of user's interest in the component part of the Web content in the information service providing system 1.

The sensor drive module 286, service execution modules 300-$p$-300-($p$+1) and information creation module 310-$p$, which are shown in FIG. 19, are selected by the module selection unit 252, and each parameter P, P' is set by the parameter setting unit 246.

In FIG. 19, the sensor drive module 286-1 operates a pulse sensor 162 worn on a user's hand or the like, detects the pulse of the user of the mobile station 2 and fixed terminal 4, and outputs the information indicating the pulse of the user to the service execution module 300-$p$.

The sensor drive module 286-2 operates a perspiration sensor 164 worn on a user's hand or the like, detects the presence or absence of user's perspiration and the amount of perspiration, and outputs the information indicating perspiration and the amount of perspiration to the service execution module 300-$p$.

The sensor drive module 286-4 operates a brain wave sensor 168 worn on a user's head or the like, detects the brain wave of the user, and outputs the information indicating the brain wave of a user to the service execution module 300-$p$.

The sensor drive module 286-13 operates an viewpoint detection sensor 186 worn on a user's head region or the like, detects which position of the Web content displayed on the output device 148 (FIG. 2) the user is viewing, and outputs the information indicating the viewpoint of the user to the service execution module 300-$p$.

The service execution module 300-($p$+2) is so-called a Web browser, and acquires Web content from a Web server 8 and displays to the user of the mobile station 2 and fixed terminal 4 through the information creation module 310 and output device 148.

Furthermore, the service execution module 300-($p$+1) notifies each position of components contained in Web content to the service execution module 300-$p$.

When the all sensors contained in the first combination of sensors 160 with a higher priority (pulse sensor 162, perspiration sensor 164, brain wave sensor 168 and viewpoint detection sensor 186; FIG. 15) are available, the service execution module 300-$p$ associates the information indicating the viewpoint of the user, which is obtained by the viewpoint detection sensor 186, with the position of the component of Web content input from the service execution module 300-($p$+2), and detects the component of Web content, which user is viewing (advertisement, banner, picture, text, etc.).

Furthermore, the service execution module 300-$p$ processes the information obtained from the pulse sensor 162, perspiration sensor 164 and brain wave sensor 168, and determines whether the user is interested in the component which the user is viewing.

When the service execution module 300 determines that the user takes an interest in any of the components of Web content, the service execution module 300-($p$+1) processes the information obtained from the pulse sensor 162, perspiration sensor 164 and brain wave sensor 168, and quantitatively calculates how much admiration the user has.

The information creation module 310 associates the component in which the user takes an interest with the information indicating the degree of his/her interest, and outputs to the output device 148 or the like as the result of the information service in a predetermined format.

When any one or more of the sensors contained in the first combination of sensors 160 with a higher priority (pulse sensor 162, perspiration sensor 164, brain wave sensor 168 and viewpoint detection sensor 186) are not available and the second combination of the sensor 160, which has a lower priority (pulse sensor 162 and perspiration sensor 164) is available, the service execution module 300-$p$ processes the information obtained by the pulse sensor 162 and perspiration sensor 164, associates it with the component of Web content displayed on the output device 148 at each point in time and its display time, and deduces in which component the user shows an interest in.

When the service execution module 300 deduces that the user takes an interest in any of the components of Web content, the service execution module 300-($p$+1) processes the information obtained from the pulse sensor 162 and perspiration sensor 164, and quantitatively calculates how much admiration the user has.

The information creation module 310 associates the component in which the user takes an interest with the information indicating the degree of his/her interest, and outputs to the output device 148 or the like as the result of the information service in a predetermined format.

When the component part of Web data which the user admires and which is detected as stated above indicates the whereabouts such as URL of information, the service execution module 300-($p$+1) acquires the information indicated by the component according to the user's predetermined operation, or, automatically, and outputs it to the output device 148 or the like through the information creation module 310.

Hereinafter, the operation of the terminal program 20 in a case where three or more combinations of sensors 160 are present for the implementation of an information service will be described.

FIG. 20 is a flow chart illustrating the operation (S20) of the terminal program 20 (FIG. 4) in a case where three or more combinations of sensors 160 are present for the implementation of an information service.

As illustrated in FIG. 20, in step 200 (S200), the terminal program 20 initializes parameter n and set it to 1 when initiating the process.

In step 202 (S202), the terminal program 20 determines whether the all sensors 160 contained in the combination of the sensors 160 (sensor drive module 286) with the n-th priority are available.

When the all sensors 160 contained in the combination of sensors 160 with the n-th priority are available, the terminal program 20 proceeds to the process of S206, and, in other cases, proceeds to the process of S204.

In step 204 (S204), the terminal program 20 increments the parameter n (n=n+1).

In step 206 (S206), the terminal program 20 performs the process to provide an information service using the combination of sensors 160 with the n-th priority.

In step 208 (S208), the terminal program 20 determines whether the combination of sensors 160 with the n+1-th priority is present.

When the combination of sensors 160 with the n+1-th priority is present, the terminal program 20 returns to the process of S202, and, in other cases, terminates the process.

In addition, it could be easily understood by a person skilled in the art that the operation of the terminal program 20 shown as the second embodiment is applicable to the first to third information services described above in the first embodiment.

The abovementioned embodiment has been presented for the purpose of illustration and description, and does not cover all of the embodiments of the disclosure of the present application.

In addition, the abovementioned embodiment is not intended to limit the technical scope of the disclosure of the present application to the disclosure, and may be varied and modified in the light of the disclosure.

In addition, the abovementioned embodiment is described after being selected so as to best describe the principle of the disclosure of the present application and its practical application, and therefore a person skilled in the art utilizes, on the basis of the disclosure of the abovementioned embodiment, the disclosure of the present application and its embodiment with various modifications so that they would be best suited to all the possible actual uses.

In addition, the technical scope of the disclosure of the present application is intended to be delimited by the description and equivalents.

INDUSTRIAL APPLICABILITY

The disclosure of the present application is available for providing a health check service.

DESCRIPTION OF SYMBOLS

1 . . . information service providing system,
100 . . . network,
102 . . . base station,
104 . . . GPS artificial satellite,
2 . . . mobile station,
4 . . . fixed terminal,
12 . . . communication processing unit,
14 . . . data processing unit,
140 . . . CPU,
142 . . . memory,
144 . . . CPU peripheral device,
146 . . . input device,
148 . . . output device,
16 . . . sensor unit,
160 . . . sensor,
162 . . . pulse sensor,
164 . . . perspiration sensor,
166 . . . blood pressure sensor,
168 . . . brain wave sensor,
170 . . . cardiac signal sensor,
172 . . . body temperature sensor,
174 . . . blood component sensor,
176 . . . GPS,
178 . . . direction sensor,
180 . . . accelerated velocity sensor,
182 . . . speed sensor,
184 . . . temperature-humidity sensor,
186 . . . viewpoint detection sensor,
188 . . . pedometer,
190 . . . other sensor,
20 . . . terminal program,
22 . . . service providing unit,
220 . . . UI,
222 . . . communication processing unit,
230 . . . application input unit,
232 . . . information output unit,
24 . . . input analyzing unit,
240 . . . input analyzing unit,
242 . . . input analyzing DB,
246 . . . parameter setting unit,
248 . . . parameter DB,
252 . . . module selection unit,
254 . . . module DB,
258 . . . information creating unit,
262 . . . information acquiring unit,
266 . . . module execution control unit,
270 . . . sensor control unit,
272 . . . sensor selection unit,
274 . . . sensor drive module DB,
278 . . . sensor output processing unit,
28 . . . sensor driving unit,
286 . . . sensor drive module,
300 . . . service execution module,
302 . . . determination data,
304 . . . map data,
310 . . . information creation module,
6 . . . module-parameter server device,
60 . . . server program,
600 . . . DB searching unit,
602 . . . module-parameter DB,
8 . . . Web server,
80 . . . Web program,
800 . . . Web data distribution unit,
802 . . . Web content DB,

The invention claimed is:

1. An information service providing system, comprising:
a module-parameter providing device;
an information service providing device which is connected to the module-parameter providing device and comprises at least a plurality of processing program modules and a plurality of output program modules; and
a content information providing device for providing content information to the information service providing device, wherein
the module-parameter providing device provides to the information service providing device, upon request from the information service providing device, components of one or more modules to be selected from the plurality of processing program modules and the plurality of output program modules, each component containing one or more of:
one or more combinations of sensor driving program modules to which a unique priority in each provision of an information service is assigned, each of which is used in each provision of the information service, one or more processing program modules for performing a process on the content information provided from the content information providing device, one or more output program modules, one or more sensor setting parameters which are set to each of the sensor driving program modules and used for its process, one or more process setting parameters which are set to each of the processing program modules and used for its process, and one or more output setting parameters which are set to each of the output program modules and used for its process, the information service providing device has an input device for accepting external input specifying one or more information services, a selector for selecting at least one of the components of the modules to be selected from the plurality of processing program modules and the plurality of output program modules to implement the one or more information services on the basis of the one or more information services and one or more of each of the components of the modules to be selected for its implementation, a receiver, to implement the one or more information services, for requesting at least one of the components of the modules to be selected from the plurality of processing program modules and the plurality of output program modules which is not present in the information service providing device to the module-parameter providing device, a plurality of sensors each of which is at least adapted to one of the sensor driving program modules contained in a combination of the one or more sensor driving program modules, a setupper for setting each of the process setting parameters and the output setting parameters to each of the processing program modules and the output program modules, and setting the sensor setting parameters to sensor driving program modules contained in a first combination to which the highest priority is assigned and in which sensors adapted to the sensor driving program modules contained in the combination are available, an execution device for responding to the one or more information services, executing the processing program modules and output program modules, executing sensor driving program modules contained in a combination to which the highest priority is assigned and in which the sensors adapted to the sensor driving program modules contained in the combination are available, and delivering information input-output between these so as to be adapted to the implementation of the one or more information services, thereby implementing the one or more information services, and an output device for outputting the result of the one or more information services, a combination of the executed sensor driving program modules drives the sensors adapted to the sensor driving program modules contained in the combination, detects and outputs sensor information, each of the executed processing program modules processes the sensor information which is input from the sensor driven by the executed sensor driving program and the provided content information, and outputs a processing result to the output program modules, and the output program modules output the processing result input from the processing program modules to the output device as the result of the one or more information services.

2. An information service providing device, comprising:

one or more combinations to which a unique priority in each provision of an information service is assigned, the information service being one of a plurality of information services, and each of the one or more combinations comprising one or more sensor driving program modules used in each provision of the information service;

one or more processing program modules for performing a process on externally accepted content information, an input device for accepting external input specifying one or more information services of the plurality of information services;

a selector for selecting a combination of the one or more sensor driving program modules contained in a first combination of the one or more combinations, to which the highest priority is assigned and in which sensors adapted to the sensor driving program modules contained in the first combination are available and the one or more processing program modules, on the basis of the plurality of information services, the one or more sensor driving program modules, and the one or more processing program modules;

a plurality of sensors each of which is adapted to at least one of the one or more sensor driving program modules contained in the first combination;

an execution device for responding to the one or more information services, executing the processing program modules and output program modules, executing sensor driving program modules contained in the first combination and in which the sensors adapted to the sensor driving program modules contained in the first combination are available, and delivering information input-output between these so as to be adapted to the implementation of the one or more information services, thereby implementing the one or more information services; and an output device for outputting the result of the one or more information services, wherein the sensor driving program modules executed by the execution device drives the sensor adapted to the sensor driving program modules contained in the first combination, detects sensor information, and outputs the sensor information, and each of the processing program modules executed by the execution device processes the sensor information which is input from the sensor driven by the sensor driving program modules executed by the execution device and the provided content information, and outputs a processing result.

3. The service providing device according to claim 2, further comprising:

one or more output program modules for processing the processing result, creating an information service result of the one or more information services in a predetermined format, and outputting the information service result to the output device, wherein the output device outputs the information service result.

4. The service providing device according to claim 2, further comprising:

one or more sensor setting parameters which are set to each of the sensor driving program modules adapted to the sensor driving program modules contained in the first combination and used for its process;

one or more process setting parameters which are set to each of the processing program modules executed by the execution device and used for its process; and a setupper for setting each of the one or more sensor setting parameters and the one or more process setting parameters to each of the sensor driving program module and the processing program modules which are adapted to these, wherein the selector further selects one or more of the sensor setting parameters and one or more of the process setting parameters to implement the specified one or more information services on the basis of the plurality of information services and one or more of the sensor setting parameters and one or more of the process setting parameters.

5. The service providing device according to claim 3, further comprising:

one or more sensor setting parameters which are set so as to be adapted to each of sensor driving program modules contained in the first combination, and are used for its process;

one or more process setting parameters which are set to each of the processing program modules executed by the execution device and used for its process;

one output setting parameter which is set to each of the output program modules executed by the execution device and used for its process; and a setupper for setting each of the sensor setting parameter, the process setting parameters and the output program modules to each of the sensor driving program module, the processing program modules and the output program modules which are adapted to these, wherein the selector further selects at least one of the one or more sensor setting parameters, the one or more of the process setting parameters, and the one or more of the output program modules to implement the one or more information services on the basis of the plurality of information services and the at least one of the one or more sensor setting parameters, the one or more of the process setting parameters, and the one or more of the output program modules, and the execution device executes the sensor driving program module, the processing program modules and the output module, and delivers information input-output between these so as to be adapted to the implementation of the one or more information services.

6. The service providing device according to claim 2, wherein, to each of the plurality of information services, priorities for its implementation are assigned, and the execution device implements only the information service which is implementable in accordance with the priority assigned to the specified information service.

7. The information service providing device according to claim 4, further comprising:

a module providing device for providing, in response to a request, one or more of:
the one or more sensor driving program modules,
the one or more processing program modules,
the one or more sensor setting parameters, and
the one or more process setting parameters; and a receiver for requesting to the module providing device for one or more of:
the one or more sensor driving program modules,
the one or more processing program modules,
the one or more sensor setting parameters, and
the one or more process setting parameters
to implement at least one of the one or more information services,
requesting this component for the module-parameter providing device, and receiving a component provided in response to this request, wherein the selector further handles, as the objects to be selected, one or more of:
the one or more sensor driving program modules,
the one or more processing program modules,
the one or more sensor setting parameters, and
the one or more process setting parameters
which are provided from the module-parameter providing device.

8. The information service providing device according to claim 5, further comprising:

a module providing device for providing, in response to a request, one or more of:
the one or more sensor driving program modules,
the one or more processing program modules,
the one or more output program modules,
the one or more sensor setting parameters,
the one or more process setting parameters, and
the one or more output setting parameters
to implement at least one of the one or more specified information services; and a receiver for requesting to the module providing device for one or more of:
the one or more sensor driving program modules,
the one or more processing program modules,
the one or more output program modules,
the one or more sensor setting parameters,
the one or more process setting parameters, and
the one or more output setting parameters
to implement at least one of the one or more information services,
requesting this component for the module-parameter providing device, and receiving a component provided in response to this request, wherein the one or more selectors further handle, as the objects to be selected, one or more of:
the one or more sensor driving program modules,
the one or more processing program modules,
the one or more output program modules,
the one or more sensor setting parameters,
the one or more process setting parameters, and
the one or more output setting parameters
which are provided from the module-parameter providing device.

9. The information service providing device according to claim 2, wherein the content data is Web data, the plurality of sensors is at least adapted to at least one of the one or more sensor driving program modules contained in the first combination, and comprise one or more sensors for detecting physical information of the viewer, each of the combinations of one or more sensor driving program modules comprises one or more sensor driving program modules for processing the physical information of the viewer detected by the plurality of sensors, at least one of the one or more processing program modules comprises a first processing program module for displaying the Web data, and a second processing program module for detecting a component contained in the Web data that interests a viewer, and a service for detecting the component contained in the Web data is provided as the information service.

10. The information service providing device according to claim 9, wherein the plurality of sensors comprise one or more viewpoint sensors for detecting a viewpoint of a viewer on the Web data, and one or more signal sensors for detecting a signal obtained from the body of the viewer of the Web data, and each of the sensor driving program modules contained in each of the combinations of the one or more sensor driving program modules is adapted to each of one or more of the viewpoint sensors and one or more of the signal sensors.

11. A method for providing an information service, comprising:

accepting external input specifying one or more information services;

selecting a first sensor driving program module contained in a first combination to which a highest priority is assigned and in which all sensors adapted to driving program modules contained in the first combination are available, within combinations to which priorities of one or more sensor driving program modules to implement the one or more information services are assigned, and one or more processing program modules to implement the one or more specified information services, on the basis of the one or more information services, the one or more sensor driving program modules, and the one or more processing program modules;

executing the one or more processing program modules, executing the first sensor driving program module contained in the first combination to which the highest priority is assigned and in which the sensors adapted to the sensor driving program modules contained in the combination are available, and delivering information input-output between these so as to be adapted to the implementation of the one or more information services, thereby implementing the one or more information services; and outputting one or more result of the one or more information services, wherein the first sensor driving program module drives one of a plurality of kind of sensors adapted to the first sensor driving program module, detects and outputs sensor information according to the kind of sensor driven by the first sensor driving program module, the one or more processing program modules processes the sensor information and outputs a processing result as the result of the one or more information services.

12. A method for providing an information service, comprising:

accepting external input specifying one or more information services;

selecting a first sensor driving program module contained in a first combination to which a highest priority is assigned and in which all sensors adapted to driving program modules contained in the combination are available from among combinations to which priorities of one or more sensor driving program modules to implement the one or more information services are assigned, and one or more processing program modules to implement the one or more information services, on the basis of the plurality of information services, the one or more sensor driving program modules, and the one or more processing program modules;

executing the one or more processing program modules, executing the first sensor driving program module contained in the first combination to which the highest priority is assigned and in which the sensors adapted to the sensor driving program modules contained in the combination are available, and delivering information input-output between these so as to be adapted to the implementation of the one or more information services, thereby implementing the one or more information services; and outputting one or more result of the one or more information services, wherein the first sensor driving program module drives one of a plurality of kind of sensors adapted to the first sensor driving program module, detects and outputs sensor information according to the kind of sensor driven by the first sensor driving program module, each of the one or more processing program modules is a program for causing a computer to execute the steps of processing the sensor information and outputting a processing result as the result of the one or more information services.

* * * * *

UNITED STATES PATENT AND TRADEMARK OFFICE
CERTIFICATE OF CORRECTION

PATENT NO. : 8,327,367 B2
APPLICATION NO. : 12/665304
DATED : December 4, 2012
INVENTOR(S) : Takano et al.

It is certified that error appears in the above-identified patent and that said Letters Patent is hereby corrected as shown below:

Title Page
Delete title page, and replace with title page. (Attached)

In the Drawings
Delete drawing sheets 4, 10, 11, 15, 18 and 19, and replace with drawing sheets 4, 10, 11, 15, 18 and 19. (Attached)

In the Specifications

In Column 22, Lines 11-15, delete "Furthermore, .... 8." and insert the same at Line 12 as a new paragraph.

In Column 22, Line 61, delete "S1-S#n)" and insert -- S#1-S#n) --, therefor.

In Column 24, Line 27, delete "S186" and insert -- 186 --, therefor.

In Column 28, Line 48, delete "DB," and insert -- DB. --, therefor.

In the Claims

In Column 31, Line 50, in Claim 6, delete "wherein," and insert -- wherein --, therefor.

In Column 32, Lines 65-66, in Claim 9, delete the extra space between "the" & "Web".

In Columns 32 & 33, Lines 67 & 1, in Claim 9, delete the extra space between "detecting" & "a".

Signed and Sealed this
Eighteenth Day of June, 2013

Teresa Stanek Rea
*Acting Director of the United States Patent and Trademark Office*

United States Patent
Takano et al.

(10) Patent No.: US 8,327,367 B2
(45) Date of Patent: *Dec. 4, 2012

(54) INFORMATION SERVICE PROVIDING SYSTEM, INFORMATION SERVICE PROVIDING DEVICE, AND METHOD THEREFOR

(75) Inventors: Kosuke Takano, Kanagawa (JP); Naofumi Yoshida, Kanagawa (JP); Shuichi Kurabayashi, Kanagawa (JP)

(73) Assignee: Empire Technology Development LLC, Wilmington, DE (US)

(*) Notice: Subject to any disclaimer, the term of this patent is extended or adjusted under 35 U.S.C. 154(b) by 279 days.

This patent is subject to a terminal disclaimer.

(21) Appl. No.: 12/665,304

(22) PCT Filed: Mar. 5, 2009

(86) PCT No.: PCT/JP2009/054140
§ 371 (c)(1),
(2), (4) Date: Dec. 17, 2009

(87) PCT Pub. No.: WO2010/100735
PCT Pub. Date: Sep. 10, 2010

(65) Prior Publication Data
US 2011/0231863 A1 Sep. 22, 2011

(51) Int. Cl.
G06F 9/46 (2006.01)
G06F 11/30 (2006.01)
G06F 11/00 (2006.01)
G01L 15/00 (2006.01)
H03F 1/26 (2006.01)

(52) U.S. Cl. ...... 718/102; 718/103; 718/106; 718/107; 702/121; 702/183; 702/184; 702/188; 702/189

(58) Field of Classification Search ............ None
See application file for complete search history.

(56) References Cited

U.S. PATENT DOCUMENTS

| 6,886,045 | B1 * | 4/2005 | Halasz et al. ............ 709/245 |
| 8,184,170 | B2 | 5/2012 | Yamaji |
| 2002/0084675 | A1 | 7/2002 | Buchanan et al. |
| 2003/0013438 | A1 | 1/2003 | Darby |
| 2003/0069752 | A1 | 4/2003 | LeDain et al. |
| 2004/0040771 | A1 | 3/2004 | Ploucha |

(Continued)

FOREIGN PATENT DOCUMENTS

JP 09-296772 11/1997

(Continued)

OTHER PUBLICATIONS

Decision of Rejection for JP 2009-545027 mailed Jun. 4, 2010 (with English translation).

(Continued)

*Primary Examiner* — Camquy Truong
(74) *Attorney, Agent, or Firm* — Foley & Lardner LLP

(57) ABSTRACT

An information service providing device selects a combination, all sensors contained in which are available and which has the highest priority, from within the combinations of sensors, which are for implementing an information service. In addition, the information service providing device selects an appropriate parameter for the sensors and processing program selected so as to be provided appropriately in response to the environment in which an information service has been implemented, and sets the parameter to these. By selecting sensors and processing program, and setting parameters, the information service providing device with only the receipt of the designation of desired information service by a user, various information services by appropriately combining various kinds of sensors and a plurality of processing programs.

12 Claims, 21 Drawing Sheets

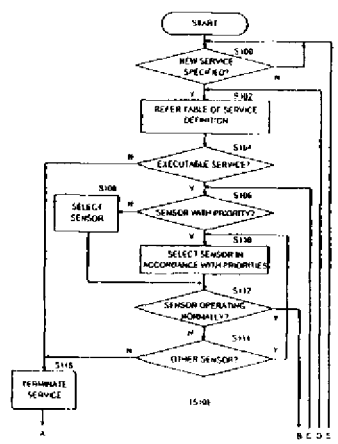

FIG. 15

| SERVICES | SENSORS FOR SERVICE AND THEIR PRIORITIES | | | | | | | | | | | | | | | | SETS OF MODULES FOR SERVICES | PRIORITIES OF SERVICES |
|---|---|---|---|---|---|---|---|---|---|---|---|---|---|---|---|---|---|---|
| | 162 | 164 | 166 | 168 | 170 | 172 | 174 | 176 | 178 | 180 | 182 | 184 | 186 | 190 | ... | 190-n | | |
| S#: (HEALTH CHECK) | 0 | 3 | 1 | 0 | 0 | 2 | 0 | 0 | 0 | 0 | 0 | 0 | 0 | 0 | | 0 | MS#1 | 2 |
| S#: (NAVIGATION) | 0 | 0 | 0 | 0 | 0 | 3 | 0 | 1 | 2 | 2 | 2 | 0 | 0 | 0 | | 0 | MS# | 1 |
| S#+1 (IMAGE INFORMATION) | 0 | 0 | 0 | 0 | 0 | 3 | 0 | 1 | 2 | 2 | 2 | 0 | 0 | 0 | | 0 | MS# | 1 |
| S#m (WEB BROWSER) | 1/2 | 0 | 0 | 1 | 0 | 0 | 0 | 0 | 0 | 0 | 0 | 0 | 1 | 0 | | 0 | MS# | 1 |
| S#n | $N_{n1}$ | $N_{n2}$ | $N_{n3}$ | $N_{n4}$ | $N_{n5}$ | $N_{n6}$ | $N_{n7}$ | $N_{n8}$ | $N_{n9}$ | $N_{n10}$ | $N_{n11}$ | $N_{n12}$ | $N_{n13}$ | $N_{n14}$ | | $N_{nx}$ | MS#n | 3 |